(12) United States Patent
Sato et al.

(10) Patent No.: US 11,119,095 B2
(45) Date of Patent: Sep. 14, 2021

(54) METHOD FOR MEASURING TYROSINE PHOSPHATASE AND TYROSINE KINASE ACTIVITY

(71) Applicant: TOKYO INSTITUTE OF TECHNOLOGY, Tokyo (JP)

(72) Inventors: Shinichi Sato, Tokyo (JP); Hiroyuki Nakamura, Tokyo (JP); Hirofumi Nakano, Tokyo (JP)

(73) Assignee: TOKYO INSTITUTE OF TECHNOLOGY, Tokyo (JP)

( * ) Notice: Subject to any disclaimer, the term of this patent is extended or adjusted under 35 U.S.C. 154(b) by 387 days.

(21) Appl. No.: 15/766,333

(22) PCT Filed: Sep. 26, 2016

(86) PCT No.: PCT/JP2016/078224
§ 371 (c)(1),
(2) Date: Apr. 5, 2018

(87) PCT Pub. No.: WO2017/061288
PCT Pub. Date: Apr. 13, 2017

(65) Prior Publication Data
US 2018/0292396 A1 Oct. 11, 2018

(30) Foreign Application Priority Data
Oct. 6, 2015 (JP) .............................. JP2015-198320

(51) Int. Cl.
*G01N 33/573* (2006.01)
*G01N 33/533* (2006.01)
(Continued)

(52) U.S. Cl.
CPC ......... *G01N 33/542* (2013.01); *C07D 237/32* (2013.01); *C12Q 1/42* (2013.01);
(Continued)

(58) Field of Classification Search
CPC .. G01N 33/533; G01N 33/542; G01N 33/573; G01N 33/5008; G01N 2333/916;
(Continued)

(56) References Cited

U.S. PATENT DOCUMENTS

| 4,748,116 A | 5/1988 | Simonsson et al. |
| 5,658,756 A * | 8/1997 | Rodan ...................... C12Q 1/42 435/193 |

(Continued)

FOREIGN PATENT DOCUMENTS

| JP | 57-501234 A | 7/1982 |
| JP | 2016-108266 A | 6/2016 |
| WO | WO-2008061108 A2 * | 5/2008 ........... C07D 237/34 |

OTHER PUBLICATIONS

Inga Kraus, Daniela Besong Agbo, Markus Otto, Jens Wiltfang & Hans Klafki, Detection and Differentiation of Threonine- and Tyrosine-Monophosphorylated Forms of ERK1/2 by Capillary Isoelectric Focusing—Immunoassay, 2015, Nature Scientific Reports, vol. 5:12767, pp. 1-10 (Year: 2015).*

(Continued)

*Primary Examiner* — Michelle F. Paguio Frising
*Assistant Examiner* — Trent R Clarke
(74) *Attorney, Agent, or Firm* — Birch, Stewart, Kolasch & Birch, LLP

(57) ABSTRACT

Provided is a method for measuring tyrosine phosphatase and tyrosine kinase activity, as a high-sensitivity measuring method, which is suitable for high throughput and which uses a compound represented by general formula (I) (in the formula, A represents a conjugated ring; L represents a linker or the like having a labeling substance at an end; $R^1$ represents a hydrogen atom or the like; and $R^2$ and $R^3$ each represent a hydrogen atom, an alkyl group or the like).

6 Claims, 7 Drawing Sheets

(51) Int. Cl.
   *G01N 33/542* (2006.01)
   *C07D 237/32* (2006.01)
   *C12Q 1/42* (2006.01)
   *C12Q 1/48* (2006.01)
   *G01N 33/50* (2006.01)
   *C07D 237/26* (2006.01)

(52) U.S. Cl.
   CPC ........... *C12Q 1/48* (2013.01); *G01N 33/5008* (2013.01); *G01N 33/533* (2013.01); *G01N 33/573* (2013.01); *C07D 237/26* (2013.01); *C12Y 301/03048* (2013.01); *G01N 2333/916* (2013.01); *G01N 2333/9121* (2013.01); *G01N 2800/042* (2013.01)

(58) Field of Classification Search
   CPC ............ G01N 2800/042; C07D 237/32; C12Y 301/03048
   See application file for complete search history.

(56) References Cited

U.S. PATENT DOCUMENTS

| | | | |
|---|---|---|---|
| 5,763,198 A * | 6/1998 | Hirth | G01N 33/68 435/15 |
| 5,917,012 A * | 6/1999 | Nishikata | C12Q 1/42 530/227 |
| 2018/0231564 A1* | 8/2018 | Mrksich | C12Q 1/00 |

OTHER PUBLICATIONS

Emil H. White, David F. Roswell, and Oliver C. Zafiriou, The Anomalous Chemiluminescence of Phthalic Hydrazide, 1968, The Journal of Organic Chemistry, vol. 34, No. 8, pp. 2462-2468 (Year: 1968).*

English translation of the Written Opinion of the International Searching Authority for PCT/JP2016/078224 (PCT/ISA/237) dated Dec. 6, 2016.

International Search Report for PCT/JP2016/078224 (PCT/ISA/210) dated Dec. 6, 2016.

Nakamura et al., "Iron-Catalyzed Tyrosine-Specific Chemical Modification of Proteins with Luminol Derivatives", The Chemical Society of Japan Koen Yokoshu, Mar. 11, 2015, vol. 95th, No. 4, total of 3 pages.

Sato et al., "Development of Tyrosine Phosphatase Screening System using Tyrosine-selective Chemical Modification", The Chemical Society of Japan, 2016, total of 3 pages.

Sato et al., "Tyrosine-Specific Chemical Modification with in Situ Hemin-Activated Luminol Derivatives", ACS Chem. Biol. 2015, vol. 10, No. 11, pp. 2633-2640.

Tokyo Institute of Technology Laboratory for Chemistry and Life Science Institute of Innovative Research, [online], Dec. 1, 2015, [retrieval date Nov. 24, 2016], pp. 1-3.

Written Opinion of the International Searching Authority for PCT/JP2016/078224 (PCT/ISA/237) dated Dec. 6, 2016.

* cited by examiner

METHOD FOR MEASURING TYROSINE PHOSPHATASE AND TYROSINE KINASE ACTIVITY

TECHNICAL FIELD

The present invention relates to a method for measuring tyrosine phosphatase and tyrosine kinase activity. The present invention also relates to a measurement kit used in this measurement method; a method for screening for a tyrosine phosphatase inhibitor or activator and a tyrosine kinase inhibitor or activator utilizing this measurement method; and a diagnostic agent utilizing this measurement method.

BACKGROUND ART

A tyrosine kinase is an enzyme that phosphorylates tyrosine residues of proteins, whereas a tyrosine phosphatase is an enzyme that catalyzes dephosphorylation of phosphorylated tyrosine residues as substrates. Tyrosine kinases and tyrosine phosphatases have important functions in vivo, and expression abnormality of these enzymes is often the cause of diseases. For example, it is known that EGFR (epidermal growth factor receptor) which is a tyrosine kinase is over-expressed in cancers such as lung cancer and colon cancer. Further, PTP1B which is a tyrosine phosphatase has been reported to be associated with diabetes. Therefore, accurately measuring the activity of tyrosine kinase and tyrosine phosphatase is important for establishing a therapeutic approach for diseases involving these enzymes.

Many methods for measuring tyrosine kinase activity are known. For example, a method using $^{32}P$ radioisotope (Non-Patent Literature 1), a method using an anti-phosphorylated antibody (Non-Patent Literature 2), a method using capillary electrophoresis (Non-Patent Literature 3) and the like are known. On the other hand, many methods for measuring tyrosine phosphatase activity are not known. As a commonly used method, a method for estimating the activity by quantifying inorganic phosphate with malachite green (Non-Patent Literature 4) or a method for quantifying a dephosphorylated product produced by reacting phosphorylated tyrosine mimic such as p-nitrophenylphosphoric acid (pNPP) with tyrosine phosphatase (Non-Patent Literature 5) is known.

CITATION LIST

Non-Patent Literature

Non-Patent Literature 1: Pike, L. J., Eakes, A. T., Krebs, E. G., Characterization of affinity-purified insulin receptor/kinase. Effects of dithiothreitol on receptor/kinase function. J. Biol. Chem., 1986, 261, 3782-3789.

Non-Patent Literature 2: Ise, N., Omi, K., Miwa, K., Honda, H., Higashiyama, S., Goishi, K., Novel monoclonal antibodies recognizing the active conformation of epidermal growth factor receptor. Biochem. Biophys. Res. Commun. 2010, 394, 685-690.

Non-Patent Literature 3: Gratz, A., Gotz, C., Jose, J., A CE-based assay for human protein kinase CK2 activity measurement and inhibitor screening. Electrophoresis 2010, 31, 634-640.

Non-Patent Literature 4: Scott, L. M., Lawrence, H. R., Sebti, S. M., Lawrence, N.J., Wu, J., Targeting protein tyrosine phosphatases for anticancer drug discovery. Curr. Pharm. Des. 2010, 16, 1843-1862.

Non-Patent Literature 5: Zhang, L., Jiang, C. S., Gao, L. X., Gong, J. X., Wang, Z. H., Li, J. Y., Li, J., Li., X. W., Guo, Y. W., Design, synthesis and in vitro activity of phidianidine B derivatives as novel PTP1B inhibitors with specific selectivity. Bioorg. Med. Chem. Lett. 2015, 26, 778-781.

SUMMARY OF INVENTION

Technical Problem

As described above, many methods for measuring tyrosine kinase activity are known, but any method has problems related to high throughput, sensitivity, and the like.

Regarding a tyrosine phosphatase, both of the above two methods have serious problems. Since the method using malachite green quantifies inorganic phosphate, there is a problem that it cannot be used under conditions in which inorganic phosphate is present (for example, in a buffer solution containing phosphate). Further, this method is unsatisfactory from the view point of measurement sensitivity. In the method using phosphorylated tyrosine mimic, since phosphorylated tyrosine mimic reacts non-selectively with a phosphatase, there is a problem that it cannot be used under the condition that phosphatases other than a tyrosine phosphatase to be measured are present.

Thus, conventional methods for measuring tyrosine phosphatase and tyrosine kinase activity have many problems. It is an object of the present invention to provide a novel means for measuring the activity in place of these troublesome methods.

Solution to Problem

In order to solve the above problems, the present inventors have conducted intensive studies and found as a result that a derivative of luminol binds to a non-phosphorylated tyrosine residue, whereas it does not bind to a phosphorylated tyrosine residue. The present invention has been achieved based on this finding.

The present invention provides the following [1] to [22].
[1] A method for measuring tyrosine phosphatase activity, the method comprising:
(1) a step of reacting a tyrosine phosphatase to be measured with a peptide containing a phosphorylated tyrosine residue(s) to dephosphorylate the phosphorylated tyrosine residue(s);
(2) a step of binding a compound represented by the following general formula (I):

[Formula 1]

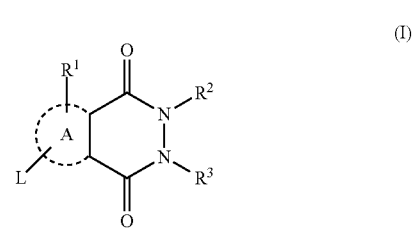

(wherein A represents a conjugated ring; L represents a hydrogen atom, or a linker having a functional group used for a click reaction or a labeling substance at the terminal, the linker existing at an arbitrary position on the conjugated ring; $R^1$ represents a hydrogen atom, one radioactive isotope existing at an arbitrary position on the conjugated ring, one functional group used for a click reaction, the functional group existing at an arbitrary position on the conjugated ring, or one or two amino group(s), acetamide group(s), hydroxyl group(s), alkyl group(s), or alkoxy group(s), the group(s) existing at an arbitrary position on the conjugated ring; $R^2$ and $R^3$ each represent a hydrogen atom, an alkyl group, or an aromatic group optionally having substituent(s)) to the dephosphorylated tyrosine residue(s) in the presence of an oxidizing agent and a metal catalyst; and (3) a step of measuring the amount of the compound represented by the general formula (I) bound to the peptide and determining the tyrosine phosphatase activity from the amount thereof.

[2] The method for measuring tyrosine phosphatase activity according to [1], wherein the compound represented by the general formula (I) is a compound represented by the following general formula (Ia):

[Formula 2]

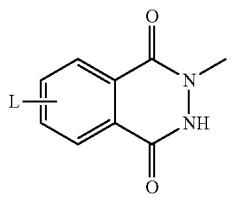

(Ia)

(wherein L is as defined above).

[3] The method for measuring tyrosine phosphatase activity according to [1] or [2], wherein the method comprises:

binding a fluorescent substance to the peptide containing a phosphorylated tyrosine residue(s);

isolating the compound represented by the general formula (I) bound to the peptide using a carrier which specifically binds to the compound represented by the general formula (I); and measuring the amount of the compound represented by the general formula (I) bound to the peptide with the fluorescent substance.

[4] The method for measuring tyrosine phosphatase activity according to [1] or [2], wherein the method comprises:

binding a fluorescent substance to the peptide containing a phosphorylated tyrosine residue(s);

binding a fluorescent substance that forms a FRET pair with the above fluorescent substance or a quencher for the above fluorescent substance to the compound represented by the general formula (I); and measuring the amount of the compound represented by the general formula (I) bound to the peptide by a change in the fluorescence of the fluorescent substance bound to the peptide and/or the fluorescent substance bound to the compound represented by the general formula (I).

[5] A kit for measuring tyrosine phosphatase activity, the kit comprising a peptide containing a phosphorylated tyrosine residue(s) and a compound represented by the following general formula (I):

[Formula 3]

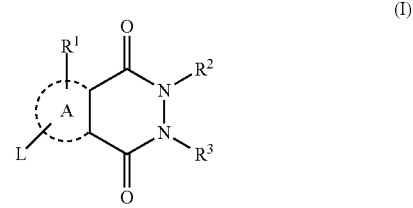

(I)

(wherein A represents a conjugated ring; L represents a hydrogen atom, or a linker having a functional group used for a click reaction or a labeling substance at the terminal, the linker existing at an arbitrary position on the conjugated ring; $R^1$ represents a hydrogen atom, one radioactive isotope existing at an arbitrary position on the conjugated ring, one functional group used for a click reaction, the functional group existing at an arbitrary position on the conjugated ring, or one or two amino group(s), acetamide group(s), hydroxyl group(s), alkyl group(s), or alkoxy group(s), the group(s) existing at an arbitrary position on the conjugated ring; $R^2$ and $R^3$ each represent a hydrogen atom, an alkyl group, or an aromatic group optionally having substituent(s)).

[6] The kit for measuring tyrosine phosphatase activity according to [5], wherein the compound represented by the general formula (I) is a compound represented by the following general formula (Ia):

[Formula 4]

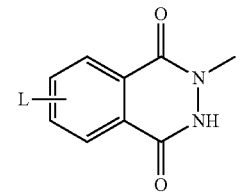

(Ia)

(wherein L is as defined above).

[7] A method for screening a tyrosine phosphatase inhibitor or activator, the method comprising:

(1) a step of contacting a peptide containing a phosphorylated tyrosine residue(s) with a tyrosine phosphatase in the presence of a test substance;

(2) a step of contacting the peptide containing a phosphorylated tyrosine residue(s) contacted with the tyrosine phosphatase with a compound represented by the following general formula (I):

[Formula 5]

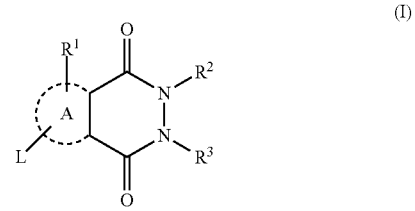

(I)

(wherein A represents a conjugated ring; L represents a hydrogen atom, or a linker having a functional group used for a click reaction or a labeling substance at the terminal, the linker existing at an arbitrary position on the conjugated ring; R¹ represents a hydrogen atom, one radioactive isotope existing at an arbitrary position on the conjugated ring, one functional group used for a click reaction, the functional group existing at an arbitrary position on the conjugated ring, or one or two amino group(s), acetamide group(s), hydroxyl group(s), alkyl group(s), or alkoxy group(s), the group(s) existing at an arbitrary position on the conjugated ring; R² and R³ each represent a hydrogen atom, an alkyl group, or an aromatic group optionally having substituent(s)) in the presence of an oxidizing agent and a metal catalyst; and (3) a step of measuring the amount of the compound represented by the general formula (I) bound to the peptide and determining the tyrosine phosphatase activity from the amount thereof.

[8] The method for screening a tyrosine phosphatase inhibitor or activator according to [7], wherein the compound represented by the general formula (I) is a compound represented by the following general formula (Ia):

[Formula 6]

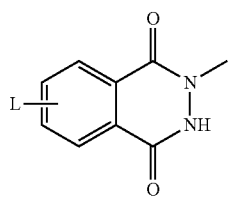

(Ia)

(wherein L is as defined above).

[9] The method for screening a tyrosine phosphatase inhibitor or activator according to [7] or [8], wherein the method comprises:
binding a fluorescent substance to the peptide containing a phosphorylated tyrosine residue(s);
isolating the compound represented by the general formula (I) bound to the peptide using a carrier which specifically binds to the compound represented by the general formula (I); and
measuring the amount of the compound represented by the general formula (I) with the fluorescent substance bound to the peptide.

[10] The method for screening a tyrosine phosphatase inhibitor or activator according to [7] or [8], wherein the method comprises:
binding a fluorescent substance to the peptide containing a phosphorylated tyrosine residue(s);
binding a fluorescent substance that forms a FRET pair with the above fluorescent substance or a quencher for the above fluorescent substance to the compound represented by the general formula (I); and
measuring the amount of the compound represented by the general formula (I) bound to the peptide by a change in the fluorescence of the fluorescent substance bound to the peptide and/or the fluorescent substance bound to the compound represented by the general formula (I).

[11] A diagnostic agent for diabetes, the agent comprising a peptide containing a phosphorylated tyrosine residue(s) and a compound represented by the following general formula (I):

[Formula 7]

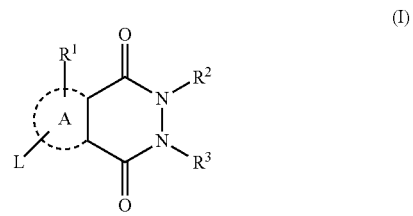

(I)

(wherein A represents a conjugated ring; L represents a hydrogen atom, or a linker having a functional group used for a click reaction or a labeling substance at the terminal, the linker existing at an arbitrary position on the conjugated ring; R¹ represents a hydrogen atom, one radioactive isotope existing at an arbitrary position on the conjugated ring, one functional group used for a click reaction, the functional group existing at an arbitrary position on the conjugated ring, or one or two amino group(s), acetamide group(s), hydroxyl group(s), alkyl group(s), or alkoxy group(s), the group(s) existing at an arbitrary position on the conjugated ring; R² and R³ each represent a hydrogen atom, an alkyl group, or an aromatic group optionally having substituent(s)).

[12] The diagnostic agent for diabetes according to [11], wherein the compound represented by the general formula (I) is a compound represented by the following general formula (Ia):

[Formula 8]

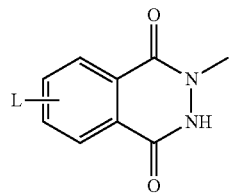

(Ia)

(wherein L is as defined above).

[13] A method for measuring tyrosine kinase activity, the method comprising:
(1) a step of reacting a tyrosine kinase to be measured with a peptide containing a non-phosphorylated tyrosine residue(s) to phosphorylate the non-phosphorylated tyrosine residue(s);
(2) a step of binding a compound represented by the following general formula (I):

[Formula 9]

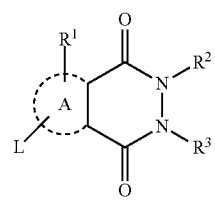

(I)

(wherein A represents a conjugated ring; L represents a hydrogen atom, or a linker having a functional group used for a click reaction or a labeling substance at the terminal, the linker existing at an arbitrary position on the conjugated ring; $R^1$ represents a hydrogen atom, one radioactive isotope existing at an arbitrary position on the conjugated ring, one functional group used for a click reaction, the functional group existing at an arbitrary position on the conjugated ring, or one or two amino group(s), acetamide group(s), hydroxyl group(s), alkyl group(s), or alkoxy group(s), the group(s) existing at an arbitrary position on the conjugated ring; $R^2$ and $R^3$ each represent a hydrogen atom, an alkyl group, or an aromatic group optionally having substituent(s)) to a tyrosine residue(s) not phosphorylated in the presence of an oxidizing agent and a metal catalyst;

(3) a step of measuring the amount of the compound represented by the general formula (I) bound to the peptide in the step (2);

(4) a step of binding the compound represented by the general formula (I) to a non-phosphorylated tyrosine residue(s) of the peptide containing a non-phosphorylated tyrosine residue(s) used in the step (1) in the presence of an oxidizing agent and a metal catalyst;

(5) a step of measuring the amount of the compound represented by general formula (I) bound to the peptide in the step (4); and (6) a step of determining the tyrosine kinase activity from the amount of the compound represented by the general formula (I) bound to the peptide measured in the step (3) and the amount of the compound represented by the general formula (I) bound to the peptide measured in the step (5).

[14] The method for measuring tyrosine kinase activity according to [13], wherein the compound represented by the general formula (I) is a compound represented by the following general formula (Ia):

[Formula 10]

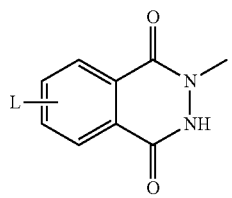

(Ia)

(wherein L is as defined above).

[15] The method for measuring tyrosine kinase activity according to [13] or [14], wherein the method comprises:
binding a fluorescent substance to the peptide containing a non-phosphorylated tyrosine residue(s);
isolating the compound represented by the general formula (I) bound to the peptide using a carrier which specifically binds to the compound represented by the general formula (I); and
measuring the amount of the compound represented by the general formula (I) bound to the peptide with the fluorescent substance.

[16] The method for measuring tyrosine kinase activity according to [13] or [14], wherein the method comprises:
binding a fluorescent substance to the peptide containing a non-phosphorylated tyrosine residue(s);
binding a fluorescent substance that forms a FRET pair with the above fluorescent substance or a quencher for the above fluorescent substance to the compound represented by the general formula (I); and
measuring the amount of the compound represented by the general formula (I) bound to the peptide by a change in the fluorescence of the fluorescent substance bound to the peptide and/or the fluorescent substance bound to the compound represented by the general formula (I).

[17] A kit for measuring tyrosine kinase activity, the kit comprising a peptide containing a non-phosphorylated tyrosine residue(s) and a compound represented by the following general formula (I):

[Formula 11]

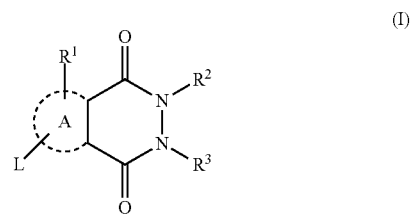

(I)

(wherein A represents a conjugated ring; L represents a hydrogen atom, or a linker having a functional group used for a click reaction or a labeling substance at the terminal, the linker existing at an arbitrary position on the conjugated ring; $R^1$ represents a hydrogen atom, one radioactive isotope existing at an arbitrary position on the conjugated ring, one functional group used for a click reaction, the functional group existing at an arbitrary position on the conjugated ring, or one or two amino group(s), acetamide group(s), hydroxyl group(s), alkyl group(s), or alkoxy group(s), the group(s) existing at an arbitrary position on the conjugated ring; $R^2$ and $R^3$ each represent a hydrogen atom, an alkyl group, or an aromatic group optionally having substituent(s)).

[18] The kit for measuring tyrosine kinase activity according to [17], wherein the compound represented by the general formula (I) is a compound represented by the following general formula (Ia):

[Formula 12]

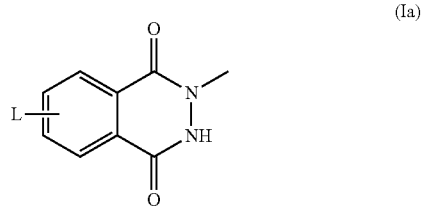

(Ia)

(wherein L is as defined above).

[19] A method for screening a tyrosine kinase inhibitor or activator, the method comprising:

(1) a step of contacting a peptide containing a non-phosphorylated tyrosine residue(s) with a tyrosine kinase in the presence of a test substance;

(2) a step of contacting the peptide containing a non-phosphorylated tyrosine residue(s) contacted with the tyrosine kinase with a compound represented by the following general formula (I):

[Formula 13]

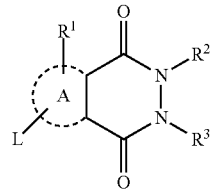
(I)

(wherein A represents a conjugated ring; L represents a hydrogen atom, or a linker having a functional group used for a click reaction or a labeling substance at the terminal, the linker existing at an arbitrary position on the conjugated ring; $R^1$ represents a hydrogen atom, one radioactive isotope existing at an arbitrary position on the conjugated ring, one functional group used for a click reaction, the functional group existing at an arbitrary position on the conjugated ring, or one or two amino group(s), acetamide group(s), hydroxyl group(s), alkyl group(s), or alkoxy group(s), the group(s) existing at an arbitrary position on the conjugated ring; $R^2$ and $R^3$ each represent a hydrogen atom, an alkyl group, or an aromatic group optionally having substituent(s)) in the presence of an oxidizing agent and a metal catalyst;
(3) a step of measuring the amount of the compound represented by the general formula (I) bound to the peptide in the step (2);
(4) a step of contacting the peptide containing a non-phosphorylated tyrosine residue(s) used in the step (1) with the compound represented by the following general formula (I) in the presence of an oxidizing agent and a metal catalyst;
(5) a step of measuring the amount of the compound represented by the general formula (I) bound to the peptide in the step (4); and
(6) a step of determining the tyrosine kinase activity from the amount of the compound represented by the general formula (I) bound to the peptide measured in the step (3) and the amount of the compound represented by the general formula (I) bound to the peptide measured in the step (5).
[20] The method for screening a tyrosine kinase inhibitor or activator according to [19], wherein the compound represented by the general formula (I) is a compound represented by the following general formula (Ia):

[Formula 14]

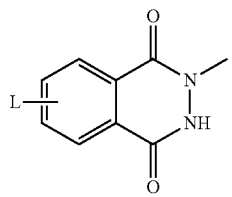
(Ia)

(wherein L is as defined above).
[21] The method for screening a tyrosine kinase inhibitor or activator according to [19] or [20], wherein the method comprises:
binding a fluorescent substance to the peptide containing a non-phosphorylated tyrosine residue(s);
isolating the compound represented by the general formula (I) bound to the peptide using a carrier which specifically binds to the compound represented by the general formula (I); and measuring the amount of the compound represented by the general formula (I) with the fluorescent substance bound to the peptide.
[22] The method for screening a tyrosine kinase inhibitor or activator according to [19] or [20], wherein the method comprises:
binding a fluorescent substance to the peptide containing a non-phosphorylated tyrosine residue(s);
binding a fluorescent substance that forms a FRET pair with the above fluorescent substance or a quencher for the above fluorescent substance to the compound represented by the general formula (I); and
measuring the amount of the compound represented by the general formula (I) bound to the peptide by a change in the fluorescence of the fluorescent substance bound to the peptide and/or the fluorescent substance bound to the compound represented by the general formula (I).

This specification includes the contents as disclosed in the specification and/or drawings of Japanese Patent Application (Patent Application No. 2015-198320), which is a priority document of the present application.

Advantageous Effects of Invention

The measuring method of the present invention can measure the activity of tyrosine phosphatase or tyrosine kinase with high accuracy. Tyrosine phosphatases and tyrosine kinases are believed to be involved in various diseases and are important targets for therapeutic agents for them. Therefore, the measuring method of the present invention is useful for development of medicines targeting these enzymes.

DESCRIPTION OF EMBODIMENTS

Figure 1:
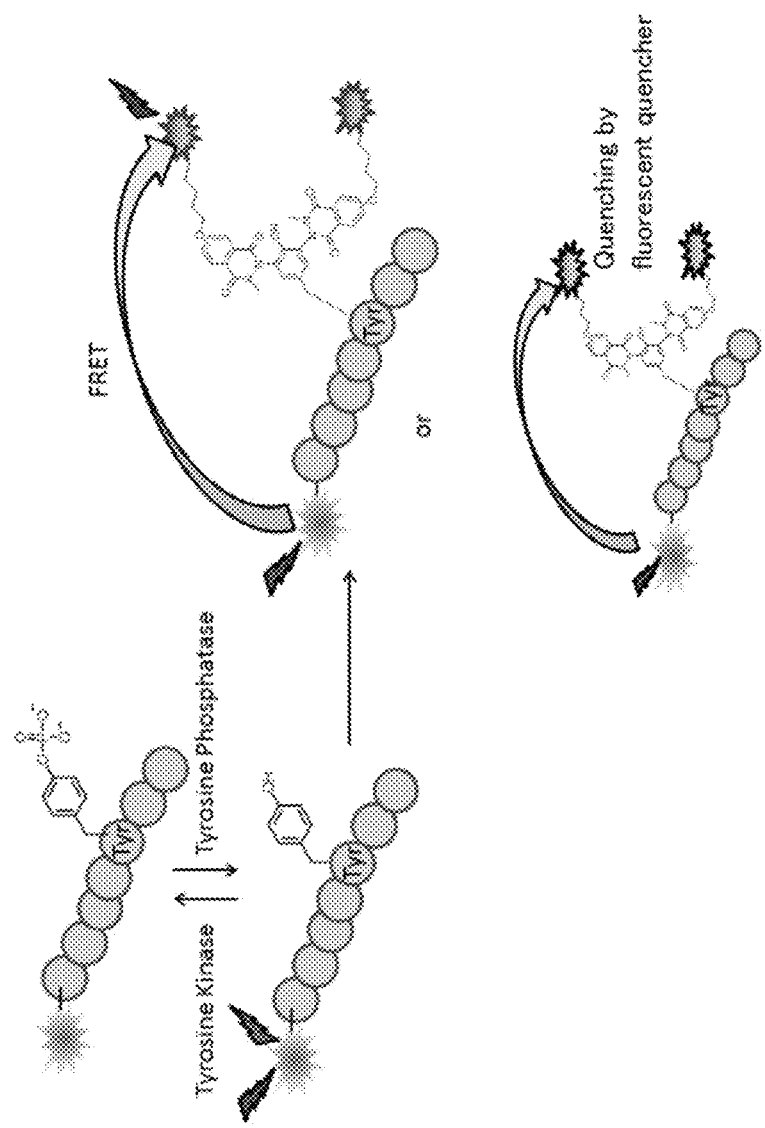
FIG. 1 is a diagram schematically illustrating a method for measuring the amount of the compound represented by formula (I) using FRET or a fluorescence quencher.

Hereinafter, the present invention will be described in detail.

In the present invention, the "alkyl group having 1 to 20 carbon atoms" is a linear or branched alkyl group having 1 to 20 carbon atoms, and examples thereof include a methyl group, an ethyl group, an n-propyl group, an iso-propyl group, a n-butyl group, an iso-butyl group, a sec-butyl group, a tert-butyl group, a pentyl group, an iso-pentyl group, a neo-pentyl group, a hexyl group, an iso-hexyl group, a heptyl group, an iso-heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, and the like.

In the present invention, the "alkyl group having 1 to 10 carbon atoms" is a linear or branched alkyl group having 1 to 10 carbon atoms, and examples thereof include a methyl group, an ethyl group, an n-propyl group, an iso-propyl group, an n-butyl group, an iso-butyl group, a sec-butyl group, a tert-butyl group, a pentyl group, an iso-pentyl group, a neo-pentyl group, a hexyl group, an iso-hexyl group, a heptyl group, an iso-heptyl group, an octyl group, a nonyl group, a decyl group, and the like.

In the present invention, the "alkyl group having 1 to 3 carbon atoms" is a linear or branched alkyl group having 1 to 3 carbon atoms, and examples thereof include a methyl group, an ethyl group, an n-propyl group, an iso-propyl group, and the like.

In the present invention, the "alkoxy group having 1 to 20 carbon atoms" is a linear or branched alkoxy group having 1 to 20 carbon atoms, and examples thereof include a methoxy group, an ethoxy group, an n-propoxy group, an iso-propoxy group, an n-butoxy group, an iso-butoxy group, a sec-butoxy group, a tert-butoxy group, a pentyloxy group, an iso-pentyloxy group, a neo-pentyloxy group, a hexyloxy group, an iso-hexyloxy group, a heptyloxy group, an iso-heptyloxy group, an octyloxy group, a nonyloxy group, a decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a nonadecyloxy group, an icosyloxy group, and the like.

In the present invention, the "alkoxy group having 1 to 10 carbon atoms" is a linear or branched alkoxy group having 1 to 10 carbon atoms, and examples thereof include a methoxy group, an ethoxy group, an n-propoxy group, an iso-propoxy group, an n-butoxy group, an iso-butoxy group, a sec-butoxy group, a tert-butoxy group, a pentyloxy group, an iso-pentyloxy group, a neo-pentyloxy group, a hexyloxy group, an iso-hexyloxy group, a heptyloxy group, an iso-heptyloxy group, an octyloxy group, a nonyloxy group, a decyloxy group, and the like.

In the present invention, the "alkoxy group having 1 to 3 carbon atoms" is a linear or branched alkoxy group having 1 to 3 carbon atoms, and examples thereof include a methoxy group, an ethoxy group, an n-propoxy group, an iso-propoxy group, and the like.

In the present invention, the "aromatic group optionally having substituent(s)" means an aromatic group having no substituent or an aromatic group having at least one substituent. Here, the "aromatic group" refers to a group obtained by removing one hydrogen atom from an aromatic compound, and examples thereof include a phenyl group, a 1-naphthyl group, a 2-naphthyl group, a pyridin-2-yl group, a pyridine-3-yl group, a pyridine-4-yl group, a pyrimidin-2-yl group, a pyrimidin-4-yl group, a pyrimidin-5-yl group, a pyrazin-2-yl group, a pyrazin-3-yl group, a pyridazin-3-yl group, a pyridazin-4-yl group, a furan-2-yl group, a furan-3-yl group, a thiophen-2-yl group, a thiophen-3-yl group, a pyrrole-1-yl group, a pyrrole-2-yl group, a pyrrole-3-yl group, a pyrazol-1-yl group, a pyrazol-3-yl group, a pyrazol-4-yl group, a pyrazol-5-yl group, an imidazol-1-yl group, an imidazol-2-yl group, an imidazol-4-yl group, an imidazol-5-yl group and the like. The substituent may be selected from the group consisting of a methyl group, a fluorine atom, a chlorine atom, a bromine atom, a hydroxy group, a methoxy group, and the like. A preferable example of the aromatic group having at least one substituent includes a phenyl group having at least one substituent. Specific examples of the phenyl group having at least one substituent include a 2-methylphenyl group, a 3-methylphenyl group, a 4-methylphenyl group, a 2,3-dimethylphenyl group, a 2,4-dimethylpheny group, a 2,5-dimethylphenyl group, a 2,6-dimethylphenyl group, a 3,4-dimethylphenyl group a 3,5-dimethylphenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2-chlorophenyl group, a 3-chlorophenyl group, a 4-chlorophenyl group, a 2,3-dichlorophenyl group, a 2,4-dichlorophenyl group, a 2,5-dichlorophenyl group, a 2,6-dichlorophenyl group, a 3,4-dichlorophenyl group, a 3,5-dichlorophenyl group, a 2-bromophenyl group, a 3-bromophenyl group, a 4-bromophenyl group, a 2,3-dibromophenyl group, a 2,4-dibromophenyl group, a 2,5-dibromophenyl group, a 2,6-dibromophenyl group, a 3,4-dibromophenyl group, a 3,5-dibromophenyl group, a 2-hydroxyphenyl group, a 3-hydroxyphenyl group, a 4-hydroxyphenyl group, a 2-methoxyphenyl group, a 3-methoxyphenyl group, a 4-methoxyphenyl group, and the like.

In the present invention, the "functional group used for a click reaction" is, for example, an azide group or an ethynyl group.

In the present invention, the "conjugated ring" means a ring having a conjugated double bond. The conjugated ring may be an aromatic ring or a non-aromatic ring. Further, the conjugated ring may be a ring composed of only carbon atoms or may be a heterocyclic ring containing an atom other than carbon such as nitrogen atom, oxygen atom, sulfur atom, and the like. Specific examples of the conjugated ring include a 6-membered ring such as a benzene ring, a 1,3-cyclohexadiene ring, a pyridine ring, a pyrimidine ring, a pyrazine ring, a pyridazine ring, and a triazine ring; a 5-membered ring such as a cyclopentadiene ring, a furan ring, a thiophene ring, a pyrrole ring, a pyrazole ring, and an imidazole ring; and the like.

In the present invention, the "radioactive isotope" can be exemplified by $^{11}C$, $^{13}N$, $^{15}O$, $^{18}F$, $^{62}Cu$, $^{68}Ga$, $^{76}Br$, $^{99m}Tc$, $^{111}In$, $^{67}Ga$, $^{201}Tl$, $^{123}I$, $^{133}Xe$, and the like. Among them, $^{18}F$ can be mentioned as a preferable radioactive isotope.

In the present invention, the "labeling substance" refers to a substance that directly or indirectly binds to a peptide or the like so that the peptide can be detected, and examples thereof include a fluorescent substance, a radioactive isotope, a substance that interact with a specific substance, and the like. Examples of the fluorescent substance include a fluorescein, a fluorescein isothiocyanate (FITC), a rhodamine, and the like. Examples of the substance that interact with a specific substance include a biotin, a substance having a structure capable of becoming an antigen of a small molecule antibody such as a dinitrophenyl group, a substance having a molecular structure capable of forming a covalent bond with a specific substance such as Halo Tag (registered trademark) or SNAP-tag (registered trademark), and the like.

In the present invention, the "group containing a labeling substance" means, for example, a moiety other than —X—

$[CH_2CH_2-Y]_m-(CH_2)_n-Z^1$ (here, X and Y each represent $CH_2$, O, NH, S, NHCO, or CO; $Z^1$ represents $N_3$ or CCH; m and n each represent an integer of 0 to 12) when the labeling substance is bound to a linker represented by $-X-[CH_2CH_2-Y]_m-(CH_2)_n-Z^1$.

[1] Method for Measuring Tyrosine Phosphatase Activity

The method for measuring tyrosine phosphatase activity of the present invention comprises:
(1) a step of reacting a tyrosine phosphatase to be measured with a peptide containing a phosphorylated tyrosine residue(s) to dephosphorylate the phosphorylated tyrosine residue(s);
(2) a step of binding a compound represented by the following general formula (I):

[Formula 15]

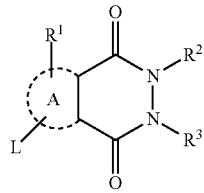

(I)

(wherein A represents a conjugated ring; L represents a hydrogen atom, or a linker having a functional group used for a click reaction or a labeling substance at the terminal, the linker existing at an arbitrary position on the conjugated ring; $R^1$ represents a hydrogen atom, one radioactive isotope existing at an arbitrary position on the conjugated ring, one functional group used for a click reaction, the functional group existing at an arbitrary position on the conjugated ring, or one or two amino group(s), acetamide group(s), hydroxyl group(s), alkyl group(s), or alkoxy group(s), the group(s) existing at an arbitrary position on the conjugated ring; $R^2$ and $R^3$ each represent a hydrogen atom, an alkyl group, or aromatic group optionally having substituent(s)) to the dephosphorylated tyrosine residue(s) in the presence of an oxidizing agent and a metal catalyst; and
(3) a step of measuring the amount of the compound represented by the general formula (I) bound to the peptide and determining the tyrosine phosphatase activity from the amount thereof.

In the conventional method using malachite green or phosphorylated tyrosine mimic, it is difficult to accurately measure tyrosine phosphatase activity in the presence of inorganic phosphate and phosphatases. Since cell homogenate or cell lysate contains inorganic phosphate and phosphatases, in the conventional method the tyrosine phosphatase contained in it cannot be measured as it is. Purification of the tyrosine phosphatase to be measured is necessary. In contrast, in the method of the present invention, the tyrosine phosphatase contained in cell homogenate or cell lysate can be measured as it is without purifying the tyrosine phosphatase. Purification of a tyrosine phosphatase from cell homogenate or cell lysate is laborious work and the method of the present invention is superior to the conventional method in that this can be omitted. Further, the fact that the activity of not a purified tyrosine phosphatase but a tyrosine phosphatase present in cell homogenate or cell lysate can be measured means that the activity can be measured in a state closer to in vivo. Therefore, the present invention is superior to the conventional method also in this point.

[1-1] Step (1)

In the step (1), a tyrosine phosphatase to be measured is reacted with a peptide containing a phosphorylated tyrosine residue to dephosphorylate the phosphorylated tyrosine residue.

The tyrosine phosphatase to be measured is not limited as long as it can dephosphorylate a phosphorylated tyrosine residue in the peptide, and examples thereof include PTP1B, SHP-1, SHP-2, TCPTP, CD45, DEP1, LAR PTP, PRL-1, LMW-PTP, and the like. Some tyrosine phosphatases have been suggested to be associated with certain diseases. Such tyrosine phosphatases include PTP that has been suggested to be associated with diabetes; SHP-2 that has been suggested to be associated with Noonan syndrome with abnormal facial skeleton formation, short stature, hypertrophic cardiomyopathy, and the like; DEP1 that has been suggested to be associated with colon cancer; and the like. These tyrosine phosphatases may be used as measurement targets.

As mentioned above, an unpurified tyrosine phosphatase can be used, but a purified tyrosine phosphatase may be used. Examples of the unpurified tyrosine phosphatase include biological samples containing a tyrosine phosphatase (e.g., cell homogenate, cell lysate, blood, plasma, urine, etc.).

As mentioned above, since some tyrosine phosphatases are associated with certain diseases, it is possible to diagnose the diseases by measuring the activity of these enzymes. As such diseases, besides diabetes described later, cancer and the like can be mentioned. Specific examples of the tyrosine phosphatase that can be used for diagnosis of a disease are shown below.

1) PTP1B

There is a report that the activation of PTP is responsible for insulin resistance (Haftchenary et al., ACS Med. Chem. Lett. 2015, 6, 982-986). From this, it is considered that insulin resistance and diabetes can be diagnosed by measuring the activity of PTP1B. Since PTP is mainly expressed in muscle, liver, or adipose tissue, PTP contained in the homogenate of this organ or tissue can be measured.

2) LAR (Leukocyte Common Antigen-Related) PTP

There is a report that the high activation of LAR PTP in muscle is involved in the development of insulin resistance (Zabolotny et al., Proc Natl Acad Sci USA, 2001, 98 (9): 5187-92). From this, it is considered that insulin resistance and diabetes can be diagnosed by measuring the activity of LAR PTP.

3) PRL-1 (Phosphatase of Regenerating Liver 1)

A method for diagnosing pancreatic cancer by collecting cells from a subject and evaluating the PRL-1 activity in the cells is known (Japanese Translation of PCT Application No. 2006-519616).

4) Low Molecular Weight Protein Tyrosine Phosphatase (LMW-PTP)

A method for diagnosing cancer by determining whether LMW-PTP is overexpressed in cell lysate obtained from a mammal is known (Japanese Translation Patent Publication No. 2006-501153).

5) SHP1

SHP1 decreases the activity of CagA that is a carcinogenic protein of *Helicobacter pylori*, and expression of this enzyme is suppressed by infection with EB virus (Saju et al., Nat Microbiol. 2016 Mar. 14; 1:16026. doi: 10.1038/nmicrobiol.2016.26.). Therefore, it is possible to diagnose the susceptibility to gastric cancer by measuring the SHP1 activity in epithelial cells of the stomach.

The peptide is not limited as long as it contains a phosphorylated tyrosine residue(s). The chain length of the peptide is preferably about 10 to 20 in view of ease of handling and the like, but a peptide that is very long and generally recognized as a "protein" rather than a "peptide" may also be used. Further, the peptide need not have any function, but a peptide or a protein having a specific function may be used. Examples of such a peptide or protein include a substrate protein for tyrosine phosphatase which has no tyrosine residue (or few tyrosine residues) modified by the reaction except for a phosphorylated tyrosine residue at the active center and a substrate protein for tyrosine phosphatase in which phosphorylated tyrosine residues are capped beforehand by a modification reaction except for a phosphorylated tyrosine residue at the active center so that a modification reaction does not proceed to the above phosphorylated tyrosine residues.

One phosphorylated tyrosine residue contained in the peptide is sufficient, but two or more phosphorylated tyrosine residues may be contained.

The peptide preferably contains only a phosphorylated tyrosine residue(s) and does not contain a non-phosphorylated tyrosine residue(s), but may also contain a non-phosphorylated tyrosine residue(s). In this case, since the compound represented by the general formula (I) binds not only to the tyrosine residue dephosphorylated by the tyrosine phosphatase activity but also to the non-phosphorylated tyrosine residue originally present, it is necessary to calculate tyrosine phosphatase activity by subtracting that amount.

The amount of tyrosine phosphatase used in this reaction is not particularly limited, but it is usually $1\times10^{-4}$ to $1\times10^{-2}$ mol, preferably $1\times10^{-3}$ to $1\times10^{-2}$ mol, per 1 mol of the peptide.

The buffer solution used in this reaction is not particularly limited, and a buffer solution containing sodium acetate, phosphate, trishydroxymethylaminomethane, a sulfonic acid type buffer (HEPES, MES, etc.), or the like can be used.

The pH during the reaction is not particularly limited, but it is usually 3 to 9, preferably 5 to 7.

The reaction temperature is not particularly limited, but it is usually 4 to 40° C., preferably 20 to 40° C.

The reaction time is not particularly limited, but it is usually 5 minutes to 24 hours, preferably 30 minutes to 2 hours.

[1-2] Step (2)

In the step (2), the compound represented by the general formula (I) is bound to the dephosphorylated tyrosine residue(s) in the presence of an oxidizing agent and a metal catalyst.

Hydrogen peroxide is usually used as the oxidizing agent, but it is not limited thereto as long as the reaction can proceed. For example, ammonium persulfate (APS), tertiary butyl peroxide, cumene peroxide, or the like may be used.

As the metal catalyst, any metal catalyst can be used as long as the reaction can proceed, but it is preferable to use a porphyrin metal complex. As the porphyrin metal complex, a porphyrin copper complex, a porphyrin cobalt complex or the like may be used, but it is preferable to use a porphyrin iron complex. As the porphyrin iron complex, in addition to the porphyrin iron complex per se, a protein including the porphyrin iron complex or the like may be used. Specific examples of the porphyrin iron complex include hemin, hemoglobin, horseradish peroxidase (HRP), myoglobin, cytochrome, and the like, among which HRP is preferably used.

In the general formula (I), A represents a conjugated ring. Although A may be a conjugated ring, it is preferably a benzene ring.

In the general formula (I), $R^1$ represents a hydrogen atom, one radioactive isotope existing at an arbitrary position on the conjugated ring, one functional group used for a click reaction, the functional group existing at an arbitrary position on the conjugated ring, or one or two amino group(s), acetamide group(s), hydroxyl group(s), alkyl group(s), or alkoxy group(s), the group(s) existing at an arbitrary position on the conjugated ring. Here, the number of carbon atoms of the alkyl group or the alkoxy group is not particularly limited, but it is preferably 1 to 20, more preferably 1 to 10, and particularly preferably 1 to 3. $R^1$ may be the above-mentioned group, but it is preferably a hydrogen atom, one amino group, one acetamide group, or one methoxy group, more preferably a hydrogen atom or one methoxy group. When two of the above substituted groups are present, each group may be the same or different. The substituted group may exist at an arbitrary position on the conjugated ring, but from the viewpoint of ease of synthesis and the like, it is preferred that the substituted group exits at a position distant from the adjacent heterocyclic ring.

In the general formula (I), $R^2$ represents a hydrogen atom, an alkyl group, or an aromatic group optionally having substituent(s). Here, the number of carbon atoms of the alkyl group is not particularly limited, but it is preferably 1 to 20, more preferably 1 to 10, and particularly preferably 1 to 3. $R^2$ may be the above-mentioned group, but it is preferably a methyl group or a phenyl group, more preferably a methyl group.

In the general formula (I), $R^3$ represents a hydrogen atom, an alkyl group, or an aromatic group optionally having substituent(s). Here, the number of carbon atoms of the alkyl group is not particularly limited, but it is preferably 1 to 20, more preferably 1 to 10, and particularly preferably 1 to 3. $R^3$ may be the above-mentioned group, but it is preferably a hydrogen atom.

In the general formula (I), L represents a hydrogen atom, a linker having a functional group used for a click reaction at the terminal, or a linker having a labeling substance at the terminal. The linker having a functional group used for a click reaction at the terminal may have any structure as long as it does not lose the binding ability of the functional group, but it is preferably a linker represented by —X—[CH$_2$CH$_2$—Y]$_m$—(CH$_2$)$_n$—Z$^1$ (here, X and Y each represent CH$_2$, O, NH, S, NHCO, or CO; Z$^1$ represents N$_3$ or CCH; m and n each represent an integer of 0 to 12), and more preferably —O—CH$_2$—CCH or —O—(CH$_2$)$_6$—N$_3$. It is to be noted that m=0 means that [CH$_2$CH$_2$—Y] does not exist and n=0 means that (CH$_2$) does not exist. The linker having a labeling substance at the terminal may have any structure as long as it does not lose the function of the labeling substance, but it is preferably a linker represented by —X—[CH$_2$CH$_2$—Y]$_m$—(CH$_2$)$_n$—Z$^2$ (here, X and Y each represent CH$_2$, O, NH, S, NHCO, or CO; Z$^2$ represents a group containing a labeling substance; m and n each represent an integer of 0 to 12).

Preferable examples of the compound represented by the general formula (I) include a compound represented by the following general formula (Ia).

[Formula 16]

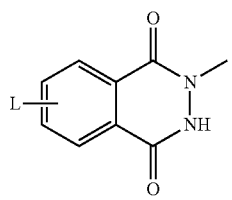

(Ia)

Here, L may exist at an arbitrary position on the benzene ring, but it preferably exists at the 6-position or the 7-position on the dihydrophthalazine ring. Further, only one kind of compound may be used as the compound represented by the general formula (Ia), but a mixture of two or more kinds of compounds may be used. For example, a mixture of a compound where L exists at the 6-position and a compound where L exists at the 7-position may be used.

The compound represented by the general formula (I) binds to the dephosphorylated tyrosine residue in the peptide, but there are cases where one molecule binds to this tyrosine residue or two molecules bind to it. When the amount of the compound represented by the general formula (I) is relatively smaller than the amount of the peptide, the oxidizing agent and the metal catalyst, two molecules of the compound represented by the general formula (I) bind to the tyrosine residue. When the amount of the compound represented by the general formula (I) is relatively larger than the amount of the peptide, the oxidizing agent and the metal catalyst, one molecule of the compound represented by the general formula (I) binds to the tyrosine residue. Therefore, by adjusting the amount ratio of the compound represented by the general formula (I), the peptide, the oxidizing agent, and the metal catalyst to be used, the number of compounds represented by the general formula (I) bound to the tyrosine residue can be controlled.

The amount of the peptide to be used is not particularly limited, but it is usually 0.001 to 1 mol, per 1 mol of the compound represented by the general formula (I). When two molecules of the compound represented by the general formula (I) binds to a tyrosine residue, the amount of the peptide is usually 0.0005 to 0.5 mol, per 1 mol of the compound represented by the general formula (I).

The amount of the oxidizing agent to be used is not particularly limited, but it is usually 1 to 100 mol, per 1 mol of the compound represented by the general formula (I). When two molecules of the compound represented by the general formula (I) binds to a tyrosine residue, the amount of the oxidizing agent is usually 1 to 100 mol, per 1 mol of the compound represented by the general formula (I).

The amount of the metal catalyst to be used is not particularly limited, but it is usually $1 \times 10^{-5}$ to $1 \times 10^{-3}$ mol, per 1 mol of the compound represented by the general formula (I). When two molecules of the compound represented by the general formula (I) binds to a tyrosine residue, the amount of the metal catalyst is usually $1 \times 10^{-5}$ to $1 \times 10^{-3}$ mol, per 1 mol of the compound represented by the general formula (I).

The buffer solution used in this reaction is not particularly limited, and a buffer solution containing a phosphate buffer solution, trishydroxymethylaminomethane, a sulfonic acid type buffer (HEPES, MES, etc.), or the like can be used. In the conventional method for measuring tyrosine phosphatase activity using malachite green, a buffer solution containing phosphate cannot be used since phosphate produced by the reaction is quantified. However, according to the method of the present invention, a buffer solution containing phosphate can be used without problems.

The pH during the reaction is not particularly limited, but it is usually 5 to 9, preferably 7 to 8.

The reaction temperature is not particularly limited, but it is usually 4 to 70° C., preferably 20 to 30° C.

The reaction time is not particularly limited, but it is usually 15 minutes to 24 hours, preferably 30 minutes to 2 hours.

The step (2) may be carried out after completion of the step (1) or may be carried out simultaneously with the step (1). That is, the compound represented by the general formula (I) may be bound to the dephosphorylated tyrosine residue by adding this compound, the oxidizing agent and the metal catalyst after the reaction between the tyrosine phosphatase and the peptide is terminated by inactivating tyrosine phosphatase or the like. Alternatively, by mixing the tyrosine phosphatase, the peptide, the compound represented by formula (I), the oxidizing agent, and the metal catalyst, the dephosphorylation of the tyrosine residue and the binding of the compound represented by the general formula (I) to the dephosphorylated tyrosine residue may occur at the same time.

[1-3] Step (3)

In the step (3), the amount of the compound represented by the formula (I) bound to the peptide is measured, and the tyrosine phosphatase activity is determined from the amount thereof.

The method for measuring the amount of the compound represented by the general formula (I) bound to the peptide is not particularly limited. For example, when the compound represented by formula (I) contains a labeling substance, it can be measured with the labeling substance. Further, when the compound represented by formula (I) contains a functional group used for a click reaction, it can be measured with a labeling substance bound to the functional group. The amount of the compound represented by the general formula (I) bound to the peptide can also be measured by the following method.

(A) Method Using a Carrier that Specifically Binds to the Compound Represented by the General Formula (I)

This method comprises: binding a fluorescent substance to a peptide containing a phosphorylated tyrosine residue; isolating a compound represented by the general formula (I) bound to the peptide using a carrier that specifically binds to the compound represented by the general formula (I); and measuring the amount of the compound represented by the general formula (I) with the fluorescent substance bound to the peptide.

As the fluorescent substance, fluorescein, FITC, rhodamine, or the like can be used.

As the carrier that specifically binds to the compound represented by the general formula (I), beads to which avidin or streptavidin is bound or the like can be used when the compound represented by the general formula (I) contains biotin. Plates on which avidin or streptavidin is immobilized can also be used.

(B) Method Using FRET

This method comprises: binding a fluorescent substance to a peptide containing a phosphorylated tyrosine residue, binding a fluorescent substance that forms a FRET pair with the above fluorescent substance to the compound represented by the general formula (I), and measuring the amount of the compound represented by the general formula (I) bound to the peptide by a change in the fluorescence of the fluorescent substance bound to the peptide and/or the fluorescent substance bound to the compound represented by the general formula (I).

FIG. 1 is a diagram schematically explaining this method using FRET.

Examples of the fluorescent substances forming a FRET pair include FITC/rhodamine, FITC/Cy3, Cy3/Cy5, and the like.

When the compound represented by the general formula (I) is bound to the dephosphorylated tyrosine residue, the fluorescence intensity of a donor fluorescent substance becomes weak and the fluorescence intensity of an acceptor fluorescent substance becomes strong. Therefore, by measuring the change in the fluorescence intensity of the donor fluorescent substance, the acceptor fluorescent substance, or both fluorescence substances, the amount of the compound represented by the general formula (I) bound to the peptide can be measured. The fluorescent substance bound to the peptide containing a phosphorylated tyrosine residue and the fluorescent substance bound to the compound represented by the general formula (I) may be a donor and an acceptor, respectively. Contrarily, the fluorescent substance bound to the peptide containing a phosphorylated tyrosine residue and the fluorescent substance bound to the compound represented by the general formula (I) may be an acceptor and a donor, respectively.

This method is suitable for high-throughput measurement of tyrosine phosphatase activity because no washing operation is required.

(C) Method Using Fluorescence Quencher

This method comprises: binding a fluorescent substance to a peptide containing a phosphorylated tyrosine residue, binding a quencher for the above fluorescent substance to a compound represented by the general formula (I), and measuring the amount of the compound represented by the general formula (I) bound to the peptide by a change in the fluorescence of the fluorescent substance bound to the peptide.

FIG. 1 is a diagram schematically explaining this method using fluorescence quencher.

Examples of the quencher include DABCYL, BHQ-1, BHQ-2, QSY-7, and the like.

When the compound represented by the general formula (I) is bound to the dephosphorylated tyrosine residue, the fluorescence intensity of the fluorescent substance bound to the peptide becomes weak. Therefore, by measuring this change in fluorescence intensity, the amount of the compound represented by the general formula (I) bound to the peptide can be measured.

This method is also suitable for high-throughput measurement of tyrosine phosphatase activity because no washing operation is required.

[2] Kit for Measuring Tyrosine Phosphatase Activity

The kit for measuring tyrosine phosphatase activity of the present invention comprises a peptide containing a phosphorylated tyrosine residue(s) and a compound represented by the general formula (I).

When the peptide containing a phosphorylated tyrosine residue and the compound represented by the general formula (I) in this kit are added to a sample containing tyrosine phosphatase, the phosphorylated tyrosine residue in the peptide is dephosphorylated by the tyrosine phosphatase, and the compound represented by the general formula (I) is bound to the dephosphorylated tyrosine residue. The tyrosine phosphatase activity can be measured by measuring this amount of the compound represented by formula (I) bound to the peptide.

The peptide containing a phosphorylated tyrosine residue and the compound represented by general formula (I) can be the same as those described in "[1] Method for measuring tyrosine phosphatase activity".

This kit may comprise something other than the peptide containing a phosphorylated tyrosine residue and the compound represented by the general formula (I).

For example, in order for the compound represented by the general formula (I) to bind to the dephosphorylated tyrosine residue, an oxidizing agent and a metal catalyst are necessary. Therefore, this kit may comprise these. Further, this kit may also comprises reagents or equipment for measuring the amount of the compound represented by the general formula (I) bound to the peptide, substances for stabilizing the peptide or the compound represented by the general formula (I), or the like.

[3] Method for Screening Tyrosine Phosphatase Inhibitor or Activator

The method for screening a tyrosine phosphatase inhibitor or activator of the present invention comprises:
(1) a step of contacting a peptide containing a phosphorylated tyrosine residue(s) with a tyrosine phosphatase in the presence of a test substance;
(2) a step of contacting the peptide containing a phosphorylated tyrosine residue(s) contacted with the tyrosine phosphatase with a compound represented by the general formula (I) in the presence of an oxidizing agent and a metal catalyst; and (3) a step of measuring the amount of the compound represented by the general formula (I) bound to the peptide and determining the tyrosine phosphatase activity from the amount thereof.

[3-1] Step (1)

In the step (1), a peptide containing a phosphorylated tyrosine residue is contacted with a tyrosine phosphatase in the presence of a test substance.

The test substance may be any substance, and either a natural product or a synthetic compound. Specific examples thereof include proteins, peptides, vitamins, hormones, polysaccharides, oligosaccharides, monosaccharides, low molecular compounds, nucleic acids (DNA, RNA, oligonucleotides, mononucleotides, etc.), lipids, and the like. Further, the test substance may be purified, but it may be unpurified cell extract, cell homogenate, cell lysate, or the like.

The amount of the test substance to be used is not particularly limited, but it is usually 10 to 10000 mol, preferably 100 to 10000 mol, per 1 mol of the tyrosine phosphatase.

The tyrosine phosphatase can be the same as that described in "[1] Method for measuring tyrosine phosphatase activity". The tyrosine phosphatases described in "[1] Method for measuring tyrosine phosphatase activity" include those causing various diseases by activation. For example, it is considered that activation of PTP1B or LAR PTP causes insulin resistance and diabetes, and activation of PRL-1 or LMW-PTP causes cancer. Therefore, inhibitors of these tyrosine phosphatases can be candidates for therapeutic or prophylactic drugs for insulin resistance, diabetes, or cancer.

The peptide containing a phosphorylated tyrosine residue can be the same as that described in "[1] Method for measuring tyrosine phosphatase activity".

Contacting the peptide containing a phosphorylated tyrosine residue with the tyrosine phosphatase may be carried out under the same conditions as the reaction of the peptide containing a phosphorylated tyrosine residue and the tyrosine phosphatase described in "[1] Method for measuring tyrosine phosphatase activity".
[3-2] Step (2)

In the step (2), the peptide containing a phosphorylated tyrosine residue contacted with the tyrosine phosphatase is contacted with a compound represented by the general formula (I) in the presence of an oxidizing agent and a metal catalyst.

The oxidizing agent, the metal catalyst, and the compound represented by the general formula (I) can be the same as those described in "[1] Method for measuring tyrosine phosphatase activity".

Contacting the peptide with the compound represented by the general formula (I) may be carried out under the same conditions as the reaction in which the compound represented by the general formula (I) is bound to the dephosphorylated tyrosine residue, which is described in "[1] Method for measuring tyrosine phosphatase activity".

The step (2) may be carried out after completion of the step (1) or may be carried out simultaneously with the step (1).
[3-3] Step (3)

In the step (3), the amount of the compound represented by the formula (I) bound to the peptide is measured, and the tyrosine phosphatase activity is determined from the amount thereof.

The amount of the compound represented by the general formula (I) bound to the peptide can be measured in the same manner as described in "[1] Method for measuring tyrosine phosphatase activity".

If the tyrosine phosphatase activity determined in the step (3) is lower than the tyrosine phosphatase activity determined in the absence of the test substance, the test substance can be judged to be a tyrosine phosphatase inhibitor. If the tyrosine phosphatase activity determined in the step (3) is higher, the test substance can be judged to be a tyrosine phosphatase activator.

[4] Diagnostic Agents for Diabetes

The diagnostic agent for diabetes of the present invention comprises a peptide containing a phosphorylated tyrosine residue(s) and a compound represented by the general formula (I).

PTP1B, a type of tyrosine phosphatase, has been reported to be associated with the onset of diabetes. Therefore, by measuring the tyrosine phosphatase activity in a sample (blood, cell lysate, etc.) taken from a subject, it can be judged whether the subject is diabetic or whether the subject has a risk of diabetes.

The peptide containing a phosphorylated tyrosine residue and the compound represented by the general formula (I) can be the same as those described in "[1] Method for measuring tyrosine phosphatase activity".

[5] Method for measuring tyrosine kinase activity

The method for measuring tyrosine kinase activity of the present invention comprises:
(1) a step of reacting a tyrosine kinase to be measured with a peptide containing a non-phosphorylated tyrosine residue(s) to phosphorylate the non-phosphorylated tyrosine residue(s);
(2) a step of binding a compound represented by the general formula (I) to a tyrosine residue(s) not phosphorylated in the presence of an oxidizing agent and a metal catalyst; (3) a step of measuring the amount of the compound represented by the general formula (I) bound to the peptide in the step (2);
(4) a step of binding the compound represented by the general formula (I) to a non-phosphorylated tyrosine residue(s) of the peptide containing a non-phosphorylated tyrosine residue(s) used in the step (1) in the presence of an oxidizing agent and a metal catalyst;
(5) a step of measuring the amount of the compound represented by general formula (I) bound to the peptide in the step (4); and
(6) a step of determining the tyrosine kinase activity from the amount of the compound represented by the general formula (I) bound to the peptide measured in the step (3) and the amount of the compound represented by the general formula (I) bound to the peptide measured in the step (5).
[5-1] Step (1)

In the step (1), a tyrosine kinase to be measured is reacted with a peptide containing a non-phosphorylated tyrosine residue to phosphorylate a non-phosphorylated tyrosine residue.

The tyrosine kinase to be measured is not limited as long as it can phosphorylate a non-phosphorylated tyrosine residue in the peptide, and examples thereof include ErbB1, ErbB2, VEGFR, ALK, and the like. Some tyrosine kinases have been suggested to be associated with certain diseases. Such tyrosine kinases include ErbB1, ErbB2, and ALK that have been suggested to be associated with cancer; VEGFR that has been suggested to be associated with pulmonary fibrosis; and the like. These tyrosine kinases may be used as measurement targets. A purified tyrosine kinase may be used, but an unpurified tyrosine kinase such as biological samples containing a tyrosine kinase may be used.

The peptide is not limited as long as it contains a non-phosphorylated tyrosine residue. The chain length of the peptide is preferably about 10 to 20 in view of ease of handling and the like, but a peptide that is very long and generally recognized as a "protein" rather than a "peptide" may also be used. Further, the peptide need not have any function, but a peptide or a protein having a specific function may be used. Examples of such a peptide or protein include a substrate protein for tyrosine kinase which has no tyrosine residue (or few tyrosine residues) modified by the reaction except for a tyrosine residue to be targeted for phosphorylation at the active center and a substrate protein for tyrosine kinase in which tyrosine residues are capped beforehand by a modification reaction except for a tyrosine residue at the active center so that a modification reaction does not proceed to the above tyrosine residues.

One non-phosphorylated tyrosine residue contained in the peptide is sufficient, but two or more non-phosphorylated tyrosine residues may be contained.

The peptide may contain only un-phosphorylated tyrosine residues or may contain both un-phosphorylated tyrosine residues and phosphorylated tyrosine residues.

The amount of tyrosine kinase used in this reaction is not particularly limited, but it is usually $1 \times 10^{-4}$ to $1 \times 10^{-2}$ mol, preferably $1 \times 10^{-3}$ to $1 \times 10^{-2}$ mol, per 1 mol of the peptide.

The buffer solution used in this reaction is not particularly limited, and a buffer solution containing a sulfonic acid type buffer (HEPES, MES, etc.), phosphate, trishydroxymethylaminomethane or the like can be used.

The pH during the reaction is not particularly limited, but it is usually 5 to 9, preferably 6 to 8.

The reaction temperature is not particularly limited, but it is usually 4 to 40° C., preferably 20 to 40° C.

The reaction time is not particularly limited, but it is usually 5 minutes to 24 hours, preferably 30 minutes to 2 hours.

[5-2] Step (2)

In the step (2), a compound represented by the general formula (I) is bound to a tyrosine residue not phosphorylated in the presence of an oxidizing agent and a metal catalyst.

The oxidizing agent, the metal catalyst, and the compound represented by the general formula (I) can be the same as those described in "[1] Method for measuring tyrosine phosphatase activity".

The reaction in which the compound represented by the general formula (I) is bound to the tyrosine residue not phosphorylated may be carried out under the same conditions as the reaction in which the compound represented by the general formula (I) is bound to the dephosphorylated tyrosine residue, which is described in "[1] Method for measuring tyrosine phosphatase activity".

[5-3] Step (3)

In the step (3), the amount of the compound represented by formula (I) bound to the peptide in step (2) is measured.

The amount of the compound represented by the general formula (I) bound to the peptide can be measured in the same manner as described in "[1] Method for measuring tyrosine phosphatase activity".

[5-4] Step (4)

In the step (4), the compound represented by formula (I) is bound to a non-phosphorylated tyrosine residue of the peptide containing a non-phosphorylated tyrosine residue used in the step (1) in the presence of an oxidizing agent and a metal catalyst.

The oxidizing agent, the metal catalyst, and the compound represented by the general formula (I) can be the same as those described in "[1] Method for measuring tyrosine phosphatase activity".

The reaction in which the compound represented by the general formula (I) is bound to the non-phosphorylated tyrosine residue may be carried out under the same conditions as the reaction in which the compound represented by the general formula (I) is bound to the dephosphorylated tyrosine residue, which is described in "[1] Method for measuring tyrosine phosphatase activity".

Since the binding reaction in this step is for comparison with the binding reaction in the step (2), it is carried out under the same conditions as the binding reaction in the step (2).

[5-5] Step (5)

In the step (5), the amount of the compound represented by formula (I) bound to the peptide in step (4) is measured.

The amount of the compound represented by the general formula (I) bound to the peptide can be measured in the same manner as described in "[1] Method for measuring tyrosine phosphatase activity".

[5-6] Step (6)

In the step (6), the tyrosine kinase activity is determined from the amount of the compound represented by the general formula (I) bound to the peptide measured in the step (3) and the amount of the compound represented by the general formula (I) bound to the peptide measured in the step (5).

By the action of tyrosine kinase, an un-phosphorylated tyrosine residue in the peptide is phosphorylated.

Since the compound represented by the general formula (I) specifically binds to a non-phosphorylated tyrosine residue, the amount of the compound represented by the general formula (I) bound to the peptide is lower when the tyrosine kinase is reacted with the peptide (measured amount in the step (3)) than when the tyrosine kinase is not reacted with the peptide (measured amount in the step (5)). Therefore, the tyrosine kinase activity can be determined from the difference between the measured amount in the step (5) and the measured amount in the step (3).

[6] Kit for Measuring Tyrosine Kinase Activity

The kit for measuring tyrosine kinase activity of the present invention comprises a peptide containing a non-phosphorylated tyrosine residue(s) and a compound represented by the general formula (I).

When the peptide containing a non-phosphorylated tyrosine residue and the compound represented by the general formula (I) in this kit are added to a sample containing tyrosine kinase, the non-phosphorylated tyrosine residue in the peptide is phosphorylated by the tyrosine kinase. Since the compound represented by the general formula (I) binds to the tyrosine residue not phosphorylated by the tyrosine kinase, the tyrosine kinase activity can be measured based on the amount of the compound represented by the general formula (I) bound to the peptide.

The peptide containing a non-phosphorylated tyrosine residue can be the same as that described in "[5] Method for measuring tyrosine kinase activity". The compound represented by general formula (I) can be the same as that described in "[1] Method for measuring tyrosine phosphatase activity".

This kit may comprise something other than the peptide containing a non-phosphorylated tyrosine residue and the compound represented by the general formula (I). For example, in order for the compound represented by the general formula (I) to bind to the tyrosine residue not phosphorylated, an oxidizing agent and a metal catalyst are necessary. Therefore, this kit may comprise these. Further, this kit may also comprises reagents or equipment for measuring the amount of the compound represented by the general formula (I) bound to the peptide, substances for stabilizing the peptide or the compound represented by the general formula (I), or the like.

[7] Method for Screening Tyrosine Kinase Inhibitor or Activator

The method for screening a tyrosine kinase inhibitor or activator of the present invention comprises:

(1) a step of contacting a peptide containing a non-phosphorylated tyrosine residue(s) with a tyrosine kinase in the presence of a test substance;

(2) a step of contacting the peptide containing a non-phosphorylated tyrosine residue(s) contacted with the tyrosine kinase with a compound represented by the general formula (I) in the presence of an oxidizing agent and a metal catalyst;

(3) a step of measuring the amount of the compound represented by the general formula (I) bound to the peptide in the step (2);

(4) a step of contacting the peptide containing a non-phosphorylated tyrosine residue(s) used in the step (1) with the compound represented by the general formula (I) in the presence of an oxidizing agent and a metal catalyst;

(5) a step of measuring the amount of the compound represented by the general formula (I) bound to the peptide in the step (4); and (6) a step of determining the tyrosine kinase activity from the amount of the compound represented by the general formula (I) bound to the peptide measured in the step (3) and the amount of the compound represented by the general formula (I) bound to the peptide measured in the step (5).

[7-1] Step (1)

In the step (1), a peptide containing a non-phosphorylated tyrosine residue is contacted with a tyrosine kinase in the presence of a test substance.

The test substance can be the same as that described in "[3] Method for screening tyrosine phosphatase inhibitor or activator". The tyrosine kinase and the peptide containing a non-phosphorylated tyrosine residue can be the same as those described in "[5] Method for measuring tyrosine kinase activity".

Contacting the peptide containing a non-phosphorylated tyrosine residue with the tyrosine kinase may be carried out under the same conditions as the reaction of the peptide containing a non-phosphorylated tyrosine residue and the tyrosine kinase described in "[5] Method for measuring tyrosine kinase activity".

[7-2] Step (2)

In the step (2), the peptide containing a non-phosphorylated tyrosine residue(s) contacted with the tyrosine kinase is contacted with a compound represented by the general formula (I) in the presence of an oxidizing agent and a metal catalyst.

The oxidizing agent, the metal catalyst, and the compound represented by the general formula (I) can be the same as those described in "[1] Method for measuring tyrosine phosphatase activity".

Contacting the peptide with the compound represented by the general formula (I) may be carried out under the same conditions as the reaction in which the compound represented by the general formula (I) is bound to the tyrosine residue not phosphorylated, which is described in "[5] Method for measuring tyrosine kinase activity".

[7-3] Step (3)

In the step (3), the amount of the compound represented by the general formula (I) bound to the peptide in the step (2) is measured.

The amount of the compound represented by the general formula (I) bound to the peptide can be measured in the same manner as described in "[1] Method for measuring tyrosine phosphatase activity".

[7-4] Step (4)

In the step (4), the peptide containing a non-phosphorylated tyrosine residue used in the step (1) is contacted with the compound represented by the general formula (I) in the presence of an oxidizing agent and a metal catalyst.

The oxidizing agent, the metal catalyst, and the compound represented by the general formula (I) can be the same as those described in "[1] Method for measuring tyrosine phosphatase activity".

Contacting the peptide with the compound represented by the general formula (I) may be carried out under the same conditions as the reaction in which the compound represented by the general formula (I) is bound to the tyrosine residue not phosphorylated, which is described in "[5] Method for measuring tyrosine kinase activity".

Since the contacting reaction in this step is for comparison with the contacting reaction in the step (2), it is carried out under the same conditions as the contacting reaction in the step (2).

[7-5] Step (5)

In the step (5), the amount of the compound represented by the general formula (I) bound to the peptide in the step (4) is measured.

The amount of the compound represented by the general formula (I) bound to the peptide can be measured in the same manner as described in "[1] Method for measuring tyrosine phosphatase activity".

[7-6] Step (6)

In the step (6), the tyrosine kinase activity is determined from the amount of the compound represented by the general formula (I) bound to the peptide measured in the step (3) and the amount of the compound represented by the general formula (I) bound to the peptide measured in the step (5).

The tyrosine kinase activity in the presence of a test substance can be determined from the difference between the measured amount in the step (5) and the measured amount in the step (3). If this activity is lower than the tyrosine kinase activity determined in the absence of the test substance, the test substance can be judged to be a tyrosine kinase inhibitor. If this activity is higher, the test substance can be judged to be a tyrosine kinase activator.

EXAMPLES

Next, the present invention will be described in more detail in accordance with examples, but the scope of the present invention should not be limited to these examples.

[Example 1] Confirmation of Phosphatase or Kinase Activity (Mass Spectrometry of Substrate Peptide)

Figure 2:
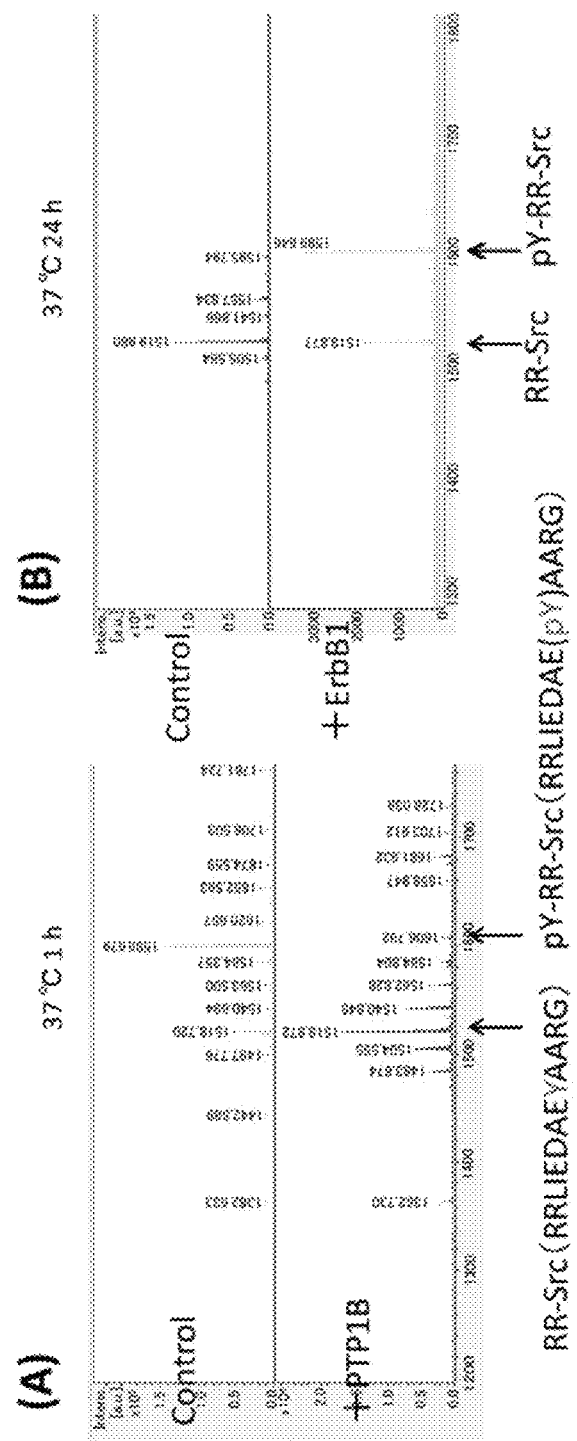
FIG. 2 Confirmation of activity of tyrosine phosphatase or tyrosine kinase by mass spectrometry. (A) shows dephosphorylation of pY-RR-Src by tyrosine phosphatase PTP1B and (B) shows phosphorylation of RR-Src by tyrosine kinase ErbB1.

(1) Confirmation of Dephosphorylation of pY-RR-Src by Tyrosine Phosphatase PTP1B To 50 µL of a 100 µM solution (dissolved in 60 mM NaOAc buffer (pH 5.5)) of pY-RR-Src (amino acid sequence: RRLIEDAE (pY) AARG, Millipore 12-217) was added 1 µg of Human recombinant PTP (Funakoshi 6301-100, Avoid repeated freeze thaw cycles), and the mixture was incubated at room temperature for 1 hour. Samples of 100 µM peptide solution before addition of PTP (control) and after incubation were diluted with 10 volumes of 0.1% TFA aqueous solution. The diluted solution (0.5-1 µM) and a 1 µM CHCA solution (0.5 mg/mL in acetonitrile: 0.1% TFA=1:1) were mixed on a MALDI-TOF-MS plate and dried at room temperature. The dephosphorylation reaction of the substrate peptide pY-RR-Src was confirmed by MALDI-TOF-MS analysis (Bruker, Ultrafle Xtreme). The MS chart after 1 hour was shown in FIG. 2(A).

(2) Confirmation of Phosphorylation of RR-Src by Tyrosine Kinase ErbB1

To 50 µL of a 100 µM solution (dissolved in 12.5 mM HEPES buffer (pH 7.4) containing 10 mM $MnCl_2$ and 1 mM ATP) of RR-Src (amino acid sequence: RRLIEDAEYAARG, Anaspec AS22581) was added 1 µg of ErbB1 (life PR7295 B, Avoid repeated freeze thaw cycles), and the mixture was incubated at 37° C. Time course of the phosphorylation of the substrate peptide was observed by the same MALDI-TOF-MS measurement method as above. The MS chart after 24 hour was shown in FIG. 2(B).

From the above results, it was suggested that the activity of tyrosine phosphatase PTP or tyrosine kinase ErbB1 as a drug discovery target could be measured if the degree of dephosphorylation of RR-Src could be measured.

[Example 2] Chemical Modification Reaction of RR-Src in Dephosphorylated State

The binding of $N_3$ compound represented by the following structure to the tyrosine residue was examined.

[Formula 17]

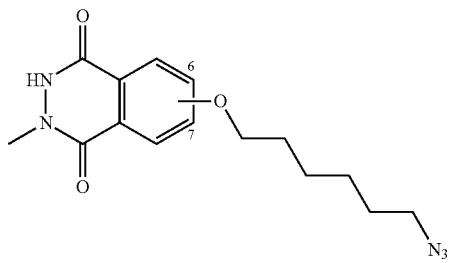

$N_3$ compound was used as a mixture of isomers in a 1:0.65 ratio of the 6-isomer:the 7-isomer.

RR-Src was dissolved in a 100 mM phosphate buffer (pH 7.4) to prepare a stock solution containing 1 mM peptide. Each reaction was carried out on a scale of 50 µL. Peptide, HRP (horse radish peroxidase, Aldrich), and $N_3$ compound were added to a 100 mM phosphate buffer (pH 7.4) in a 0.6 ml Eppendorf tube to prepare a solution containing 100 µM peptide, 50 nM HRP, and 0.1-1 mM $N_3$ compound at the final concentration.

Figure 3:
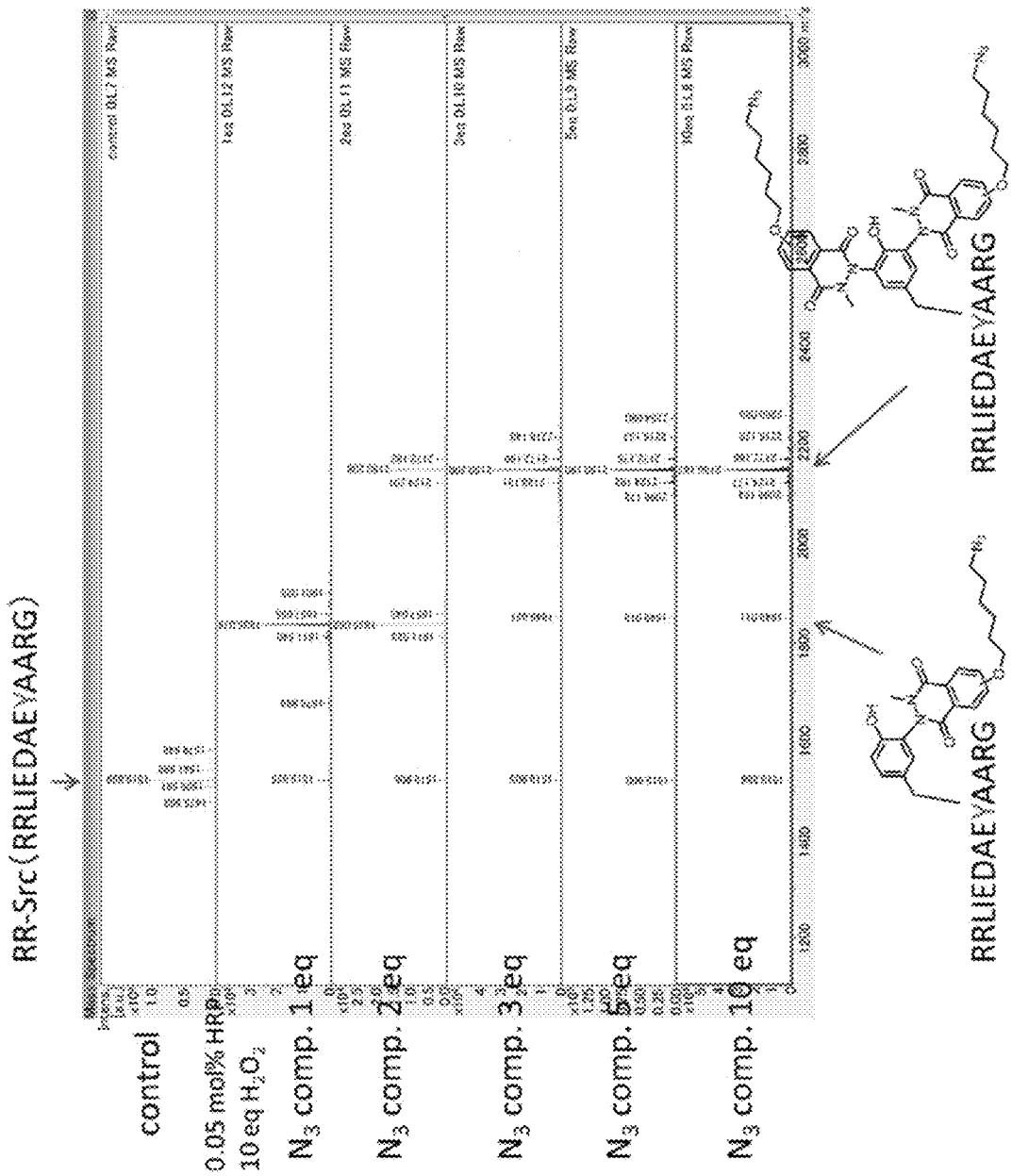
FIG. 3 Confirmation of binding of $N_3$ compound to RR-Src by mass spectrometry.

Hydrogen peroxide was added to the solution so that the final concentration became 1 mM. Then the mixture was vortexed and was allowed to stand at room temperature for 1 hour. The mixture was diluted to a concentration of 1/10 in an aqueous solution containing 10 mM DTT and 0.1% TFA. The diluted solution (0.5-1 µM) and a 1 µM CHCA solution (0.5 mg/mL in acetonitrile: 0.1% TFA=1:1) were mixed on a MALDI-TOF-MS plate and dried at room temperature. Covalent bond formation reaction was confirmed by MALDI-TOF-MS analysis (Bruker, Ultrafle Xtreme) (FIG. 3). MS/MS has demonstrated that $N_3$ compound binds specifically to tyrosine residues and that two $N_3$ compounds bind to one tyrosine residue.

As a result, it was found that the reaction almost quantitatively proceeded even under the condition that $N_3$ compound was 1 equivalent to the peptide, and that up to two $N_3$ compounds can be bound to one tyrosine residue.

[Example 3] Chemical Modification Selective for Peptides in Non-Phosphorylated State Each reaction was carried out on a scale of 50 µL. Peptides (RR-Src and pY-RR-Src), HRP (horse radish peroxidase, Aldrich), and $N_3$ compound were added to a 100 mM phosphate buffer (pH 7.4) in a 0.6 ml Eppendorf tube to prepare a solution containing 100 µM RR-Src, 100 µM pY-RR-Src, 50 nM HRP, and 1 mM $N_3$ compound at the final concentration.

Hydrogen peroxide was added to the solution so that the final concentration became 1 mM. Then the mixture was vortexed and was allowed to stand at room temperature for 1 hour. The mixture was diluted to a concentration of 1/10 in an aqueous solution containing 10 mM DTT and 0.1% TFA. The diluted solution (0.5-1 µM) and a 1 µM CHCA solution (0.5 mg/mL in acetonitrile: 0.1% TFA=1:1) were mixed on a MALDI-TOF-MS plate and dried at room temperature. Covalent bond formation reaction was confirmed by MALDI-TOF-MS analysis (Bruker, Ultrafle Xtreme) (FIG. 4).

Figure 4:
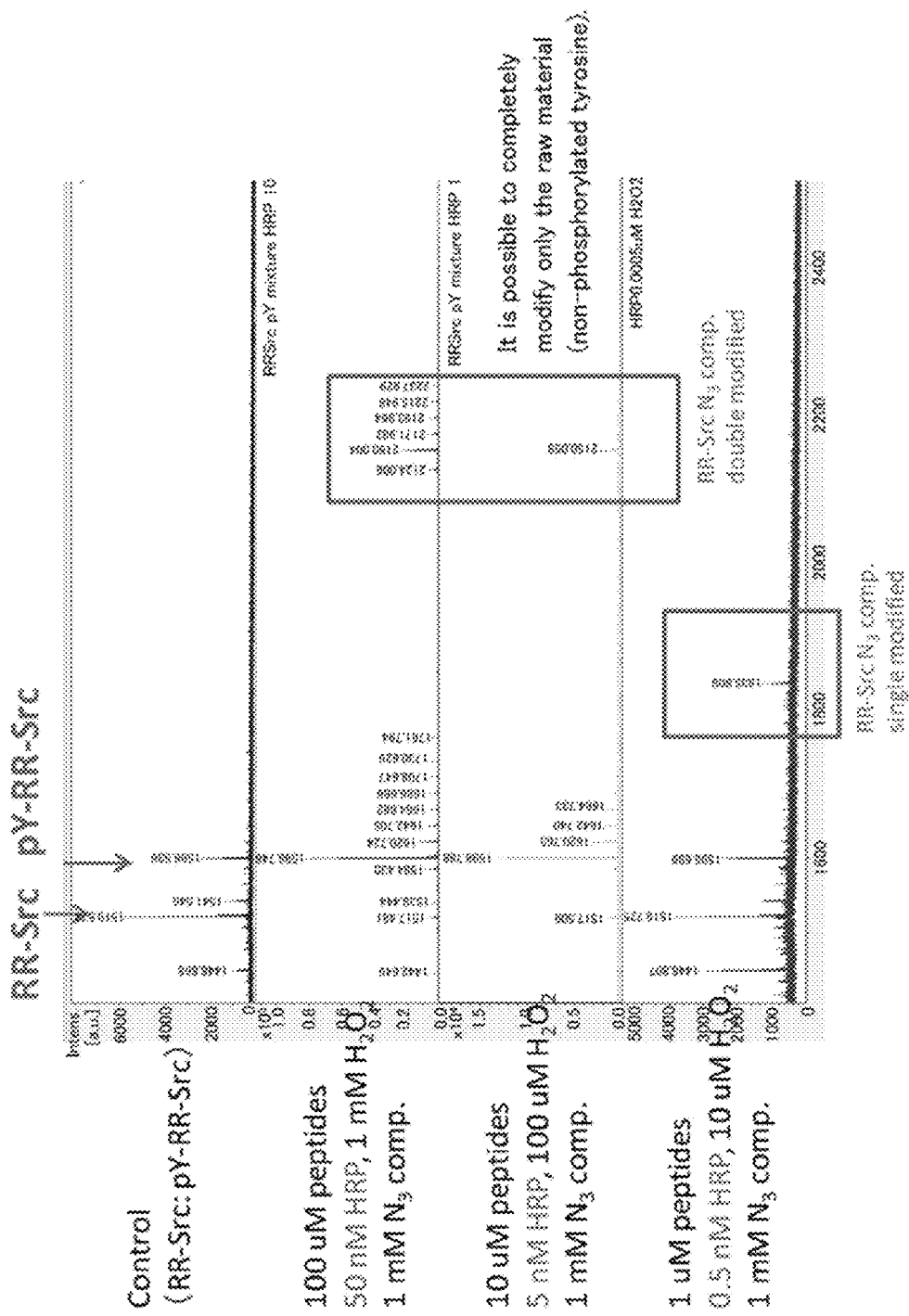
FIG. 4 Covalent modification to mixture of RR-Src and pY-RR-Src.

The results in FIG. 4 revealed that the covalent modification reaction did not proceed to the phosphorylated substrate peptide (pY-RR-Src) and proceeded specifically only to the dephosphorylated substrate peptide (RR-Src). It was also suggested that nearly quantitative reactions were possible even under reaction conditions with a peptide concentration of 10 µM.

[Example 4] Biotinylation of Chemically Modified Peptide (Click Reaction)

To a peptide solution (containing 100 µM peptide and 1 mM $N_3$ compound) having the same composition as "$N_3$ comp. 10 eq" shown in FIG. 3 was added 2 mM DBCO-biotin (Aldrich), and the mixture was incubated at 37° C. for 1 hour. The solution (1 µM) and a 1 µM CHCA solution (0.5 mg/mL in acetonitrile: 0.1% TFA=1:1) were mixed on a MALDI-TOF-MS plate and dried at room temperature. Covalent bond formation reaction was confirmed by MALDI-TOF-MS analysis (Bruker, Ultrafle Xtreme) (lower part of FIG. 5).

Figure 5:
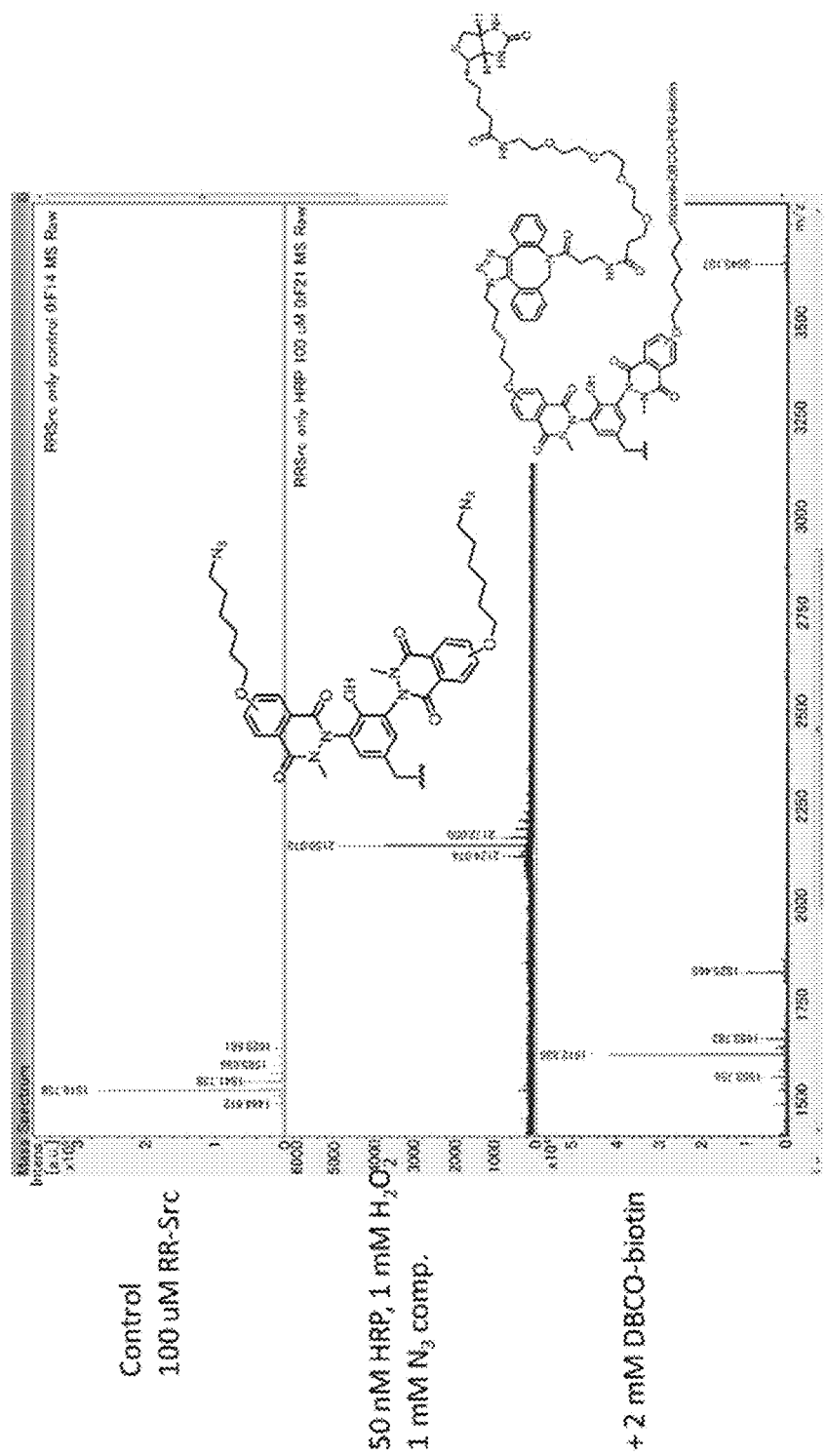
FIG. 5 Introduction of biotin site to peptide modified with $N_3$ compound by click reaction. The upper chart shows a MS chart of only RR-Src (the same as the control in FIG. 3), the middle chart shows a MS chart of a mixed solution of $N_3$ compound and RR-Src (the same as "$N_3$ comp. 10 eq" in FIG. 3), and the lower chart shows a MS chart of a solution obtained by adding DBCO-biotin to the mixed solution of $N_3$ compound and RR-Src.

In FIG. 3, it was found that chemical modification of RR-Src by $N_3$ compound quantitatively proceeded. In FIG. 5, it was further suggested that the click reaction quantitatively proceeded also to the modified peptide, and that the biotin structure could be introduced.

[Example 5] Detection of Chemically Modified Non-Phosphorylated Substrate Peptide To a solution (100 µM peptide) of $N_3$ compound-modified RR-Src or biotin-modified RR-Src prepared by the method described in Examples 2 or 4 was added a 1 M DMSO solution of FITC (5-Isothiocyanatofluorescein, TCI) so that the final concentration of FITC became 4 mM, and the mixture was incubated at room temperature for 1 hour. A solution of fluorescently labeled $N_3$ compound-modified RR-Src and a solution of fluorescently labeled biotin-modified RR-Src were named Sample 1 and Sample 2, respectively. From each sample, a solution containing 100 pmol of peptide was collected. The solution was stirred with 200 µg of FG-beads Streptavidin beads (TAMAGAWA SEIKI Co., Ltd.) for 30 minutes in 100 mM phosphate buffer (pH 7.4) to bind the biotin-modified peptide to the magnetic beads. Thereafter, the beads were washed three times with 1 mL of a 100 mM phosphate buffer (pH 7.4) and suspended in 100 µL of this buffer. The suspension was subjected to fluorescence measurement with a plate reader (TECAN, Ex/Em=485/510 nm).

Figure 6:
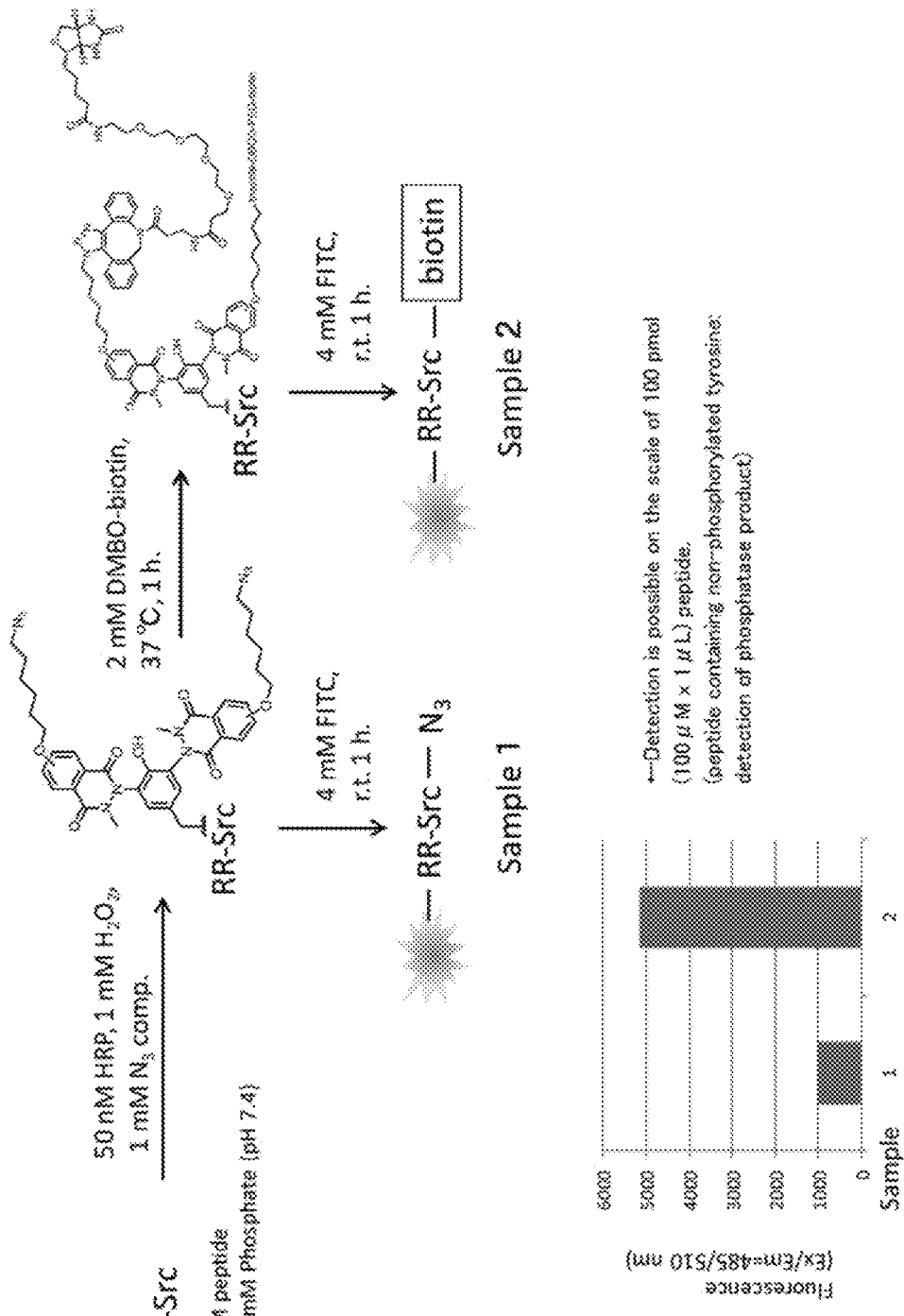
FIG. 6 High sensitive detection of chemically modified peptides by fluorescent labeling.

Since FITC forms a covalent bond with the amino group in the peptide, it binds to the N-terminal amino group in RR-Scr and can fluorescently label the peptide. Comparison of the fluorescence of Samples 1 and 2 suggested that this method, in which biotin-modified peptides were captured with beads and detected with fluorescence, was detectable even under conditions with 100 pmol of non-phosphorylated protein as a substrate (FIG. 6).

[Comparative Example] Detection Limit of Malachite Green Method (Conventional Method)

To compare with malachite green method, which is one of the few conventional methods for measuring tyrosine phosphatase, the detection limit of Tyrosine Phosphatase Assay System (Promega) was calculated experimentally.

In the present invention, a peptide containing a tyrosine residue in a non-phosphorylated state is detected, whereas in the above assay kit, free inorganic phosphate generated at 1 equivalent per a peptide as a result of a dephosphorylation reaction by phosphatase is quantified. Therefore, there is a limitation that a buffer containing phosphate cannot be used in this assay.

Figure 7:
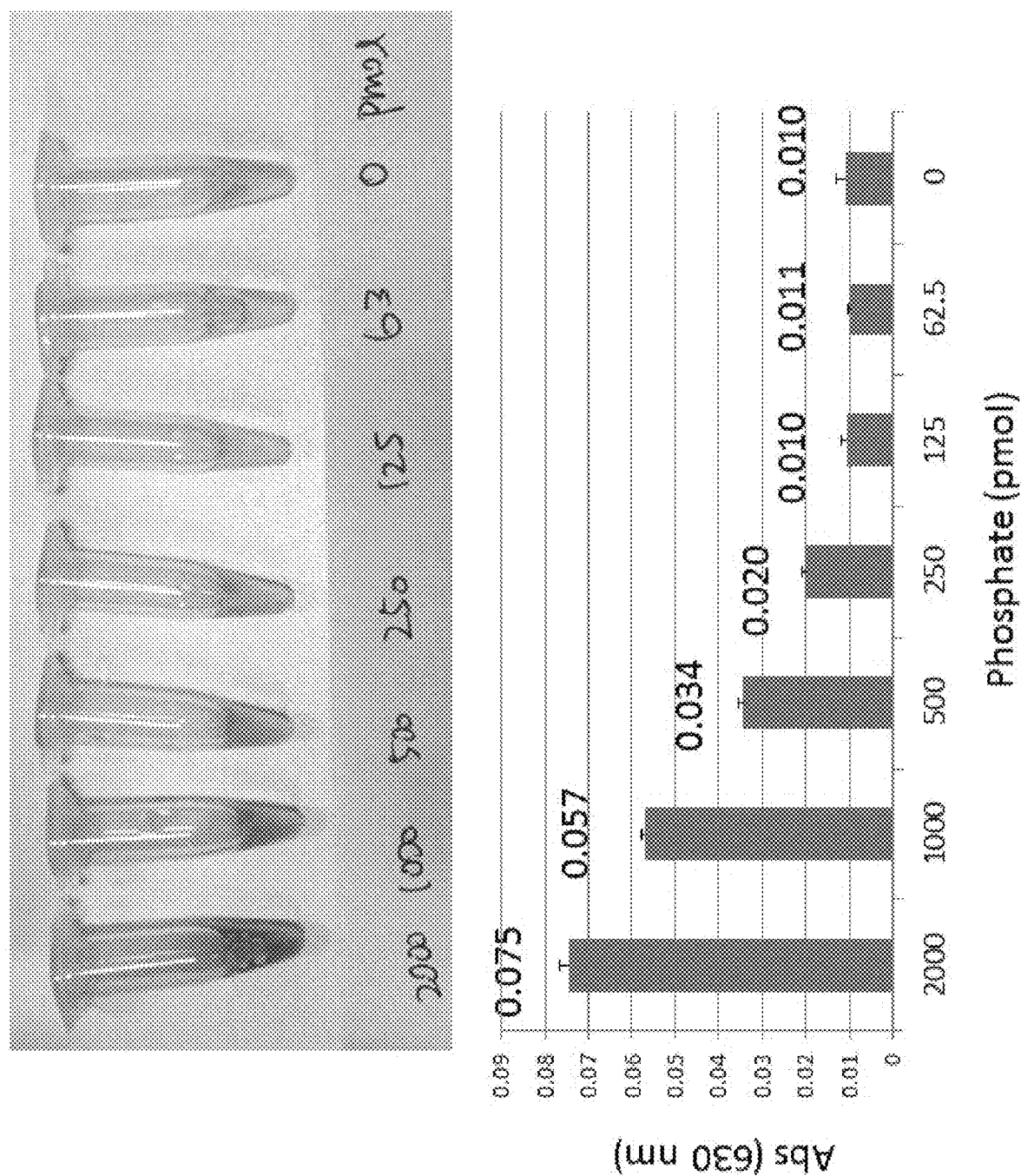
FIG. 7 Detection limit of inorganic phosphate by malachite green method (kit manufactured by Promega).

According to the protocol of the above assay kit, the detection effective range of inorganic phosphate is described as 200-4000 pmol. According to the protocol, colorimetric determination of inorganic phosphate using malachite green/molybdenum reagent was actually carried out (absorbance measurement at 630 nm). The result showed that the detection limit was predictably about 200 pmol as shown in FIG. 7. Therefore, it is considered that the present invention exceeds the conventional method also in terms of detection sensitivity.

All the publications, patents, and patent applications cited in the present specification are incorporated into the present specification by reference in their entirety.

INDUSTRIAL APPLICABILITY

Since the method for measuring tyrosine phosphatase and tyrosine kinase activity of the present invention is useful for development of new pharmaceutical products, it can be used in industrial fields such as the pharmaceutical industry.

The invention claimed is:

1. A method for directly measuring tyrosine phosphatase activity, the method comprising:
   (1) a step of reacting a tyrosine phosphatase to be measured with a peptide containing a phosphorylated tyrosine residue(s) to dephosphorylate the phosphorylated tyrosine residue(s);
   (2) a step of binding a compound represented by the following formula (Ia):

[Formula Ia]

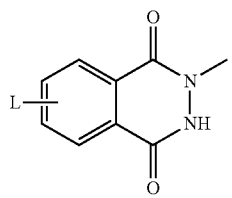

(Ia)

(wherein L represents a hydrogen atom, or a linker having a functional group used for a click reaction or a labeling substance at the terminal, the linker existing at an arbitrary position on the benzene ring to the dephosphorylated tyrosine residue(s) in the presence of an oxidizing agent and a metal catalyst; and
   (3) a step of measuring the amount of the compound represented by formula (Ia) bound to the peptide and determining the tyrosine phosphatase activity from the amount thereof.

2. The method for measuring tyrosine phosphatase activity according to claim 1, wherein the method comprises:
   binding a fluorescent substance to the peptide containing a phosphorylated tyrosine residue(s); isolating the compound represented by formula (Ia) bound to the peptide using a carrier which specifically binds to the compound represented by formula (Ia); and measuring the amount of the compound represented by formula (Ia) bound to the peptide with the fluorescent substance.

3. The method for measuring tyrosine phosphatase activity according to claim 1, wherein the method comprises:
   binding a fluorescent substance to the peptide containing a phosphorylated tyrosine residue(s); binding a fluorescent substance that forms a FRET pair with the above fluorescent substance or a quencher for the above fluorescent substance to the compound represented by formula (Ia); and measuring the amount of the compound represented by formula (Ia) bound to the peptide by a change in the fluorescence of the fluorescent substance bound to the peptide and/or the fluorescent substance bound to the compound represented by formula (Ia).

4. The method for directly measuring tyrosine phosphatase activity according to claim 1, wherein the tyrosine phosphatase is a purified tyrosine phosphatase.

5. The method for directly measuring tyrosine phosphatase activity according to claim 1, wherein the tyrosine phosphatase is present in a cell homogenate or cell lysate.

6. The method for directly measuring tyrosine phosphatase activity according to claim 1, wherein the tyrosine phosphatase activity occurs extracellular.

* * * * *